United States Patent [19]

Blaszczak

[11] Patent Number: 4,918,185
[45] Date of Patent: Apr. 17, 1990

[54] PROCESS FOR CARBON-CARBON BOND FORMATION AT THE C-4 POSITION OF 3-ACYLAMINOAZETIDINONES AND PRODUCTS AND STARTING MATERIALS THEREFOR

[75] Inventor: Larry C. Blaszczak, Indianapolis, Ind.

[73] Assignee: Eli Lilly and Company, Indianapolis, Ind.

[21] Appl. No.: 195,552

[22] Filed: May 19, 1988

Related U.S. Application Data

[60] Division of Ser. No. 99,803, Sep. 22, 1987, Pat. No. 4,771,135, which is a continuation of Ser. No. 613,111, May 22, 1984, abandoned.

[51] Int. Cl.$^4$ .................. C07D 205/08; C07D 403/12; C07D 417/12; C07D 409/12
[52] U.S. Cl. .................................................... 540/364
[58] Field of Search .......................... 540/364

[56] References Cited

U.S. PATENT DOCUMENTS

| 4,383,945 | 5/1983 | Hashimoto et al. | 260/239 A |
| 4,446,146 | 5/1984 | Southgate et al. | 474/274 |

FOREIGN PATENT DOCUMENTS

| 68466 | 1/1983 | European Pat. Off. | |
| 2071650A | 9/1981 | United Kingdom | 540/355 |
| 2091724A | 8/1982 | United Kingdom | 540/355 |

OTHER PUBLICATIONS

Branch et al, Tet. Letters 24, 1649–52 (1983).
Koller, Tet. Letters 23, 1545–1548 (1982).
G. E. Keck et al., *J. Amer. Chem. Soc.*, 104, 5829 (1982).
G. E. Keck et al., *J. Org. Chem.*, 47, 3590 (1982).
G. E. Keck et al., *J. Orgmet. Chem.*, 248, C21 (1983).
M. Aratani et al., *Tet. Letters,* 23, 3921 (1982).
G. A. Kraus et al., *J. Chem. Soc., Chem. Commun.*, 134 (1982).

*Primary Examiner*—Mark L. Berch
*Attorney, Agent, or Firm*—Joseph A. Jones; Leroy Whitaker; Bruce J. Barclay

[57] ABSTRACT

This invention relates to certain 3-acylamino-4-(2'-substituted or unsubstituted allyl)-azetidinone products of the formula

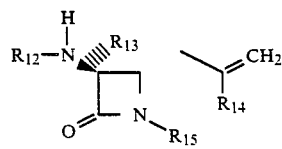

wherein
$R_{12}$ is an acyl group;
$R_{13}$ is hydrogen or methoxy;
$R_{14}$ is hydrogen, $C_1$ to $C_6$ alkyl or cycloalkyl, phenyl, phenyl-$C_1$ to $C_4$ alkyl or (protected carboxy)-methyl; and
$R_{15}$ is hydrogen or an amino protecting group.

6 Claims, No Drawings

PROCESS FOR CARBON-CARBON BOND FORMATION AT THE C-4 POSITION OF 3-ACYLAMINOAZETIDINONES AND PRODUCTS AND STARTING MATERIALS THEREFOR

This application is a division, of application Ser. No. 099,803, filed Sept. 22, 1987 now U.S. Pat. No. 4,771,135 which is a continuation of application Ser. No. 613,111, filed May 22, 1984, now abandoned.

SUMMARY OF THE INVENTION

This invention relates to a process for substituting the C-4 position of a 3-acylaminoazetidinone with an allyl or 2-(substituted)allyl group under free radical conditions outlined in the following formula:

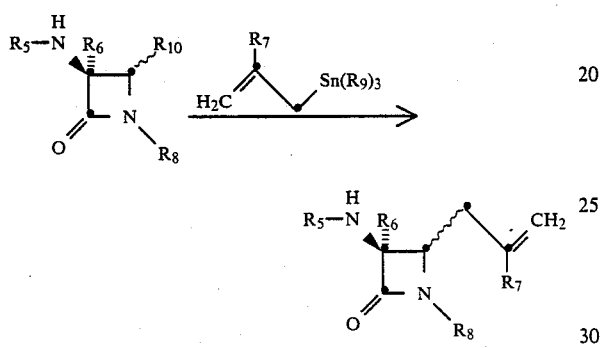

In the above formula, the symbols $R_5$, $R_6$, $R_7$, $R_8$, $R_9$ and $R_{10}$ have the same meaning as the identical symbols associated with Scheme I, below.

Certain starting materials for the process of this invention are a second aspect of the present invention. These starting materials are depicted by the following formula:

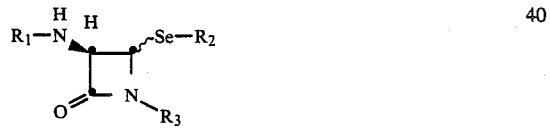

In the above formula, $R_1$, $R_2$ and $R_3$ have the same meaning as defined for the identical symbols in formula I, below.

The third aspect of the present invention is certain products of the above process, as depicted by the following formula

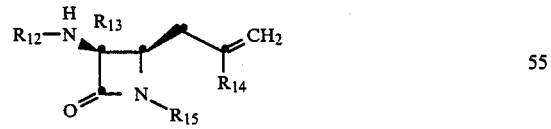

In the above formula the symbols $R_{12}$, $R_{13}$, $R_{14}$ and $R_{15}$ have the same meaning as the identical symbols in formula V, below.

DETAILED DESCRIPTION OF THE INVENTION

This invention relates to three general aspects: (1) 3-acylamino-4-(substituted selenyl)azetidinone starting materials, (2) a process converting these starting materials to 3-acylamino-4-(allyl or substituted allyl)azetidinones and (3) certain of the (3,4)-cis-3-acylamino-4-(allyl or substituted allyl)azetidinone products of the process.

I.

THE INVENTION IN GENERAL; DEFINITION OF TERMS

Specifically, the starting material aspect of the invention are 4-(R,S)-(substituted selenyl)azetidinone compounds represented by the following formula I

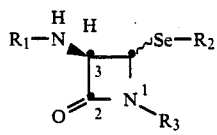

In the above formula I, $R_1$ is an acyl group of the formula

wherein
$R_a$ is
(a) $C_1$ to $C_7$ alkyl, cyanomethyl, 4-protected-amino-4-protected carboxybutyl; or
(b) $C_1$ to $C_6$ alkoxy, allyloxy, phenoxy, benzyloxy or 4-methoxybenzyloxy; or
(c) the group $R_b$, wherein $R_b$ is phenyl or substituted phenyl, wherein the substituents are one or two halogens, protected hydroxy, cyano, trifluoromethyl, $C_1$ to $C_4$ alkyl, $C_1$ to $C_4$ alkoxy, protected amino, protected carboxy, protected carboxymethyl, protected hydroxymethyl or protected aminomethyl; or
(d) an arylalkyl group of the formula $R_b-(O)_m-CH_2-$ wherein $R_b$ is an defined above and m is 0 or 1; or
(e) a substituted arylalkyl group of the formula

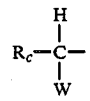

wherein $R_c$ is $R_b$ as defined above, plus thien-2-yl, thien-3-yl, fur-2-yl and fur-3-yl; W is protected hydroxy, protected carboxy or protected amino; or
(f) a heteroarylmethyl group of the formula $R_d-CH_2-$ wherein $R_d$ is thien-2-yl, thien-3-yl, fur-2-yl, fur-3-yl, thiazol-2-yl, tetrazol-5-yl, or tetrazol-1-yl;
$R_2$ is $C_1$ to $C_4$ alkyl, phenyl, substituted phenyl, 1-naphthyl or 2-naphthyl; and
$R_3$ is hydrogen, an amino-protecting group or a group of the formula

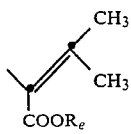

wherein $R_e$ is a carboxy protecting group.

As used in defining compounds of formula I, the term "$C_1$ to $C_7$ alkyl" refers to methyl, ethyl, n-propyl, n-butyl, iso-butyl, pentyl, n-hexyl, n-heptyl, cyclohexyl, and like aliphatic hydrocarbon chains. The term "$C_1$ to $C_6$ alkoxy" refers to groups such as methoxy, ethoxy, n-propoxy, iso-propoxy, n-butoxy, iso-butoxy, t-butoxy, valeroxy, hexyloxy, and the like. The preferred group encompassed by this term is t-butoxy. The term "$C_1$ to $C_4$ alkyl" refers to methyl, ethyl, n-propyl, n-butyl, iso-butyl and the like. The term "$C_1$ to $C_4$ alkoxy" refers to groups such as methoxy, ethoxy, n-propoxy, iso-propoxy, iso-butoxy, t-butoxy and the like.

Terms such as "amino-protecting group" and "protected amino" denote an amino moiety bonded to one of the commonly employed amino-blocking groups such as the trimethylsilyl group, the tert-butoxycarbonyl group (t-BOC), the (tert-butyl)dimethylsilyl group, the benzyloxycarbonyl group, the 4-methoxybenzyloxycarbonyl group, the 4-nitrobenzyloxycarbonyl group, 2,2,2-trichloroethoxycarbonyl group, or the 1-carbomethoxy-2-propenyl group formed with methylacetoacetate. Similar amino-protecting groups such as those described by J. W. Barton in "Protective Groups In Organic Chemistry", J. F. W. McOmie, Ed., Plenum Press, New York, N.Y., 1973, Chapter 2, and T. W. Greene, "Protective Groups In Organic Synthesis", John Wiley and Sons, New York, N.Y., 1981, Chapter 7, are suitable. A requirement of these groups is that one skilled in the art is able to substitute and remove them from the amino group(s) without disrupting the remainder of the molecule. Furthermore, these groups should prevent the amino group from reacting with the solvents, products, reagents and other substrates of the process aspect of the invention, described below.

Terms such as "protected carboxy" and "carboxy-protecting group" refer to a carboxy function bonded to one of the carboxylic acid substituents commonly employed to block or protect the carboxylic acid functionality while reacting other functional groups on the compound. Examples of such carboxylic acid protecting groups include methyl, tert-butyl, 4-methoxybenzyl, diphenylmethyl, benzyl, 2,4,6-trimethoxybenzyl, trityl, 4-methoxytrityl, 4,4'-dimethoxytrityl, and 4,4',4"-trimethoxytrityl and the like moieties. The species of carboxy-protecting group employed is not critical so long as the derivatized carboxylic acid is stable to the condition of subsequent reaction(s) and can be removed at the appropriate point without disrupting the remainder of the molecule. In particular, neither the protected carboxy function or the protecting group itself should react with the solvents, reagents, products and other substrate molecules of the process aspect of the invention described below. Preferred carboxylic acid protecting groups include methyl, benzyl, diphenylmethyl and 4-methoxybenzyl. Similar carboxy-protecting groups such as those described by E. Haslam in "Protective Groups in Organic Chemistry" J. F. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5 are suitable.

Terms such as "protected hydroxy" and "hydroxy protecting group", means hydroxy moieties bonded to conventional groups stable to the reaction conditions in the process aspect of the instant invention and/or the subsequent steps employing the products of the process in the synthesis of antibiotic compounds. Such groups include the formyl group, the benzhydryl group, the trityl group, the trimethylsilyl group, and the like. Similar hydroxy-protecting groups such as those described by C. B. Reese and E. Haslam in "Protective Groups in Organic Chemistry" J. F. W. McOmie, Ed., Plenum Press, New York, N.Y., 1973, Chapters 3 and 4, and T. W. Greene, "Protective Groups in Organic Synthesis", John Wiley and Sons, New York, N.Y., 1981, Chapter 2 shall be recognized as suitable. All that is further required of these groups is that one skilled in the art is able to substitute and remove them from the hydroxy group(s) without disrupting the remainder of the molecule.

In the foregoing definitions, hydroxy, amino, and carboxy protecting groups are not exhaustively defined. Many such protecting groups are well known in the art and the use of other groups equally applicable to the process and compounds of the present invention, such as those described in J. F. W. McOmie, "Protective Groups in Organic Chemistry", Plenum Press, 1973, and T. W. Green, "Protective Groups in Organic Synthesis", John Wiley and Sons, New York, N.Y. 1981, are suitable. Thus, the "protecting groups" discussed in the specification are not in and of themselves the distinguishing feature of the instant invention.

The term "substituted phenyl" refers to a mono- or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3-chloro-4-bromophenyl, 2-fluorophenyl and the like; a mono- or di(protected hydroxy)phenyl group such as 4-(protected hydroxy)phenyl, 3-(protected hydroxy)phenyl, 2,4-di(protected hydroxy)phenyl and the like; a mono- or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono- or disubstituted lower alkoxyphenyl group, for example, 2,6-dimethoxyphenyl, 4-methoxyphenyl, 3-ethoxyphenyl, 4-isopropoxyphenyl, 4-(t-butoxy)phenyl, 3-ethoxy-4-methoxyphenyl; a mono- or disubstituted (protected amino)phenyl group such as 4-(protected amino)phenyl or 2,5-di-(protected amino)phenyl; a mono- or disubstituted trifluoromethylphenyl group such as 4-trifluoromethylphenyl, 3,4-di-(trifluoromethyl)phenyl, and the like; a mono- or disubstituted protected carboxyphenyl group, such as 4-(protected carboxy)phenyl, 2-(protected carboxy)phenyl, 3-(protected carboxy)phenyl, 2,4-di(protected carboxy)phenyl, and the like; a phenyl ring sibstituted by one or two protected carboxymethyl groups, such as 2-(protected carboxymethyl)phenyl, 3-(protected carboxymethyl)phenyl, 4-(protected carboxymethyl)phenyl, 2,3-di(protected)carboxymethylphenyl, and the like; a phenyl moiety that is mono- or disubstituted by protected hydroxymethyl, resulting in benzyl alcohol type moieties, for example, 2-(protected hydroxymethyl)phenyl, 4-(protected hydroxymethyl)phenyl, 3-(protected hydroxymethyl)phenyl, 3,4-di(protected hydroxymethyl)phenyl, and the like; phenyl groups mono- or disubstituted by (protected-amino)methyl groups, resulting in benzylamine type moieties, e.g. 2-(protected-aminomethyl)phenyl, 4-(protected-aminomethyl)phenyl, 2,3-di(protected-aminomethyl)phenyl, and the like. The term "substituted phenyl" also represents disubstituted phenyl groups wherein substituents can be different, for example, 3-methyl-4(protected hydroxy)phenyl, 3-chloro-4-(protected hydroxy)phenyl, 2-methoxy-4-bromophenyl, 4-ethyl-2-(protected hydroxy)phenyl, 2-(protected hydroxy)-4-chlorophenyl, 3-trifluoromethyl-4-(protected hydroxy)phenyl, 2-(protected carboxy)-4-ethoxyphenyl, 2-(protected-aminomethyl)-4-(protected hydroxymethyl)phenyl, 4-(protected carboxymethyl)-2-methylphenyl, 3-(protected hydroxymethyl)-4-chlorophenyl, and like disubstituted phenyl groups bearing different substituents.

Illustrative of the acyl groups

when $R_a$ is a group of the formula $R_b-(O)_m-CH_2-$, m is 0 and $R_b$ is phenyl or substituted phenyl as defined above, are phenylacetyl, 4-chlorophenylacetyl, 3-(protected hydroxy)phenylacetyl, 4-(protected hydroxy)-3-methylphenylacetyl, 4-(protected hydroxy)-phenylacetyl, 4-bromophenylacetyl, 4-ethoxyphenylacetyl, 3,4-dimethoxyphenylacetyl, and the like; and when m is 1, representative acyl groups are phenoxyacetyl, 3-(protected hydroxy)phenoxyacetyl, 4-(protected hydroxy)phenoxyacetyl, 4-chlorophenoxyacetyl, 3,4-dichlorophenoxyacetyl, 2-chlorophenoxyacetyl, 4-methoxyphenoxyacetyl, 2-ethoxyphenoxyacetyl, 3,4-dimethylphenoxyacetyl, 4-isopropylphenoxyacetyl, 4-methyl-2-(protected carboxy)phenoxyacetyl, 4-(protected-aminomethyl)-phenoxyacetyl, 4-(protected carboxyphenoxy)acetyl, 4-(protected carboxymethyl)phenoxyacetyl, 3-(trifluoromethyl)phenoxyacetyl, 2-(protected hydroxymethyl)phenoxyacetyl, 2-(protected-amino)phenoxyacetyl, and like acyl groups.

The preferred acyl groups when $R_a$ is a group of the formula $R_b-(O)_m-CH_2-$ occurs when $R_b$ is phenyl. The more preferred groups occur when m is 1 and $R_b$ is phenyl.

Illustrative of the acyl groups

wherein $R_a$ is a substituted arylalkyl group of the formula

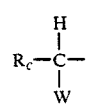

as defined above are the hydroxy-substituted arylalkyl groups such as the 2-(protected hydroxy)-2-phenylacetyl group of the formula

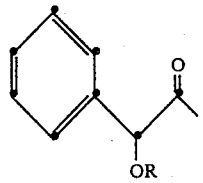

(wherein R is a hydroxy protecting group) and similar groups wherein the phenyl ring is substituted, for example, 2-(protected hydroxy)-2-(4-methoxyphenyl)acetyl, 2-(protected hydroxy)-2-(3-chloro-4-(protected hydroxy)phenyl)acetyl, 2-(protected hydroxy)-2-(4-(protected hydroxy)phenyl)acetyl, 2-(protected hydroxy)2-(3-bromophenyl)acetyl, 2-(protected hydroxy)-2-(3,5-dichloro-4-(protected carboxy)phenyl)acetyl, 2-(protected hydroxy)-2-(3-chloro-4-methoxyphenyl)acetyl, 2-(protected hydroxy)-2-(3-chlorophenyl)acetyl, and like groups. Also included are the 2-(protected carboxy)phenylacetyl group of the formula

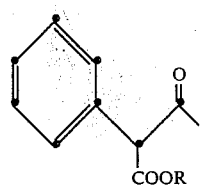

(wherein R is a carboxy protecting group) and similar groups wherein the phenyl ring is substituted, for example, 2-(tert-butoxycarbonyl)-2-phenylacetyl, 2-(benzyloxycarbonyl)-2-(4-chlorophenyl)acetyl, 2-(protected carboxy)-2-(4-methoxyphenyl)acetyl, 2-(protected carboxy)-2-(4-protected hydroxyphenyl)acetyl, and like groups. Further included are the 2-(protected amino)2-phenylacetyl group of the formula

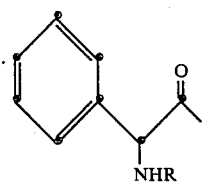

(wherein R is an amino protecting group) and similar groups wherein the phenyl ring is substituted, for example, 2-(protected-amino)-2-(4-chlorophenyl)acetyl, 2-(protected-amino)-2-(4-(protected hydroxy)phenyl)acetyl, and like acyl groups. Finally, groups such as 2-(protected-amino)-2-(thien-2-yl)acetyl, 2-(protected-amino)-2-(2-fur-2-yl)acetyl, and the like are also illustrative of the above substituted arylalkyl group.

Representative of the acyl group

when $R_a$ is a heteroarylmethyl group of the formula

are a thien-2-ylacetyl group, a thien-3-ylacetyl group, a fur-2-ylacetyl group, fur-3-ylacetyl group, thiazol-2-ylacetyl group of the formula

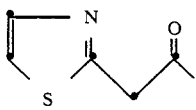

a 2-(1-tetrazolyl)acetyl group of the formula

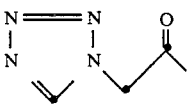

or a 2-(5-tetrazolyl)acetyl group of the formula

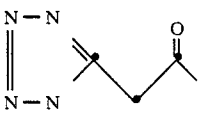

The preferred substituents of the compound represented by formula I are as follows:

$R_1$ is an acyl group of the formula

wherein
$R_a$ is
(1) $C_1$ to $C_6$ alkoxy, allyloxy, phenoxy, benzyloxy, 4-methoxybenzyloxy; and
(2) an arylalkyl group of the formula $R_b-(O)_m-CH_2-$;

$R_2$ is $C_1$ to $C_4$ alkyl, phenyl, 1-naphthyl or 2-naphthyl; and
$R_3$ is hydrogen or tri(alkyl)silyl.

More preferred substitutents are encompassed within the above set of preferred substitutents for the compounds of formula I when:

$R_1$ is a group of the formula

wherein
$R_a$ is:
(a) t-butoxy, allyloxy, or benzyloxy; or
(b) an arylalkyl group of the formula $R_b-(O)_m-CH_2-$ wherein
$R_b$ is phenyl; and
$R_2$ is $C_1$ to $C_4$ alkyl or phenyl.

The most preferred substituents are encompassed within the above group of more preferred substitutents for the compound represented by formula I when:

$R_1$ is a group of the formula

wherein
(1) $R_a$ is t-butoxy; or
(2) an arylalkyl group of the formula $R_b-(O)_m-CH_2-$ wherein
$R_b$ is phenyl and m is one; and
$R_2$ is methyl or phenyl; and
$R_3$ is hydrogen, trimethylsilyl or (t-butyl)dimethylsilyl.

The second aspect of this invention comprises a process for preparing 4-allyl and 4-(substituted allyl)azetidinones set forth below in general Scheme I:

Scheme I

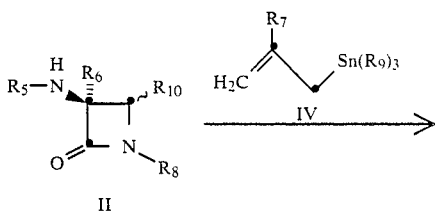

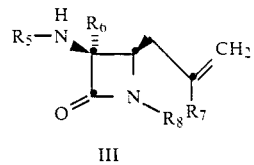

In the above Scheme I,
$R_5$ is an acyl group of the formula

wherein
$R_f$ is
(a) $C_1$ to $C_7$ alkyl, cyanomethyl, 4-protected amino-4-protected carboxybutyl; or
(b) $C_1$ to $C_6$ alkoxy, allyloxy, phenoxy, benzyloxy or 4-methoxybenzyloxy; or
(c) the group $R_g$, wherein $R_g$ is phenyl or substituted phenyl, wherein the substituents are one or two halogens, protected hydroxy, cyano, trifluoromethyl, $C_1$ to $C_4$ alkyl, $C_1$ to $C_4$ alkoxy, protected amino, protected carboxy, protected carboxymethyl, protected hydroxymethyl or protected aminomethyl; or
(d) an arylalkyl group of the formula $R_g-(O)_m-CH_2-$ wherein m is 0 or 1; or
(e) a substituted arylalkyl group of the formula

wherein $R_h$ is $R_g$ as defined above plus thien-2-yl, thien-3-yl, fur-2-yl and fur-3-yl; and W is protected hydroxy, protected carboxy, protected amino; or (f) a heteroarylmethyl group of the formula $R_i$—CH$_2$— wherein $R_i$ is thien-2-yl, thien-3-yl, fur-2-yl, fur-3-yl, thiazol-2-yl, tetrazol-5-yl, or tetrazol-1-yl;

$R_6$ is hydrogen or methoxy;

$R_7$ is hydrogen, $C_1$ to $C_6$ alkyl or cycloalkyl, phenyl, phenyl($C_1$ to $C_4$)alkyl, or (protected carboxy)methyl;

$R_8$ is hydrogen, an amino-protecting group, or a group of the formula

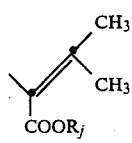

wherein $R_j$ is a carboxy protecting group;

$R_9$ is independently $C_1$ to $C_6$ alkyl or phenyl;

$R_{10}$ is chloro, bromo, iodo, or a group of the formula

—Se—$R_{11}$ or

—S—$R_{11}$ wherein $R_{11}$ is $C_1$ to $C_4$ alkyl, phenyl, substituted phenyl, 1-naphthyl or 2-naphthyl; provided that when $R_{10}$ is a group of the formula

—S—$R_{11}$, $R_8$ is other than a group of the formula

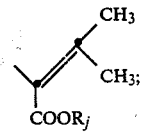

further provided that when $R_{10}$ is a group of the formula

—S—$R_{11}$ or

—Se—$R_{11}$ $R_6$ is other than methoxy.

The conditions for the process depicted in the above Scheme I entails reacting a β-lactam substrate (II) with between about 1.0 to about 6 molar equivalents of the allyl in tin compound (IV) in the presence of a free radical initiator.

The solvents used for the above process are substantially anhydrous aromatic hydrocarbons or 1,2-dimethoxyethane. The reaction is carried out under a substantially inert atmosphere.

In the description of the above Scheme I, the terms "$C_1$ to $C_7$ alkyl", "$C_1$ to $C_6$ alkoxy", "$C_1$ to $C_4$ alkyl", "$C_1$ to $C_4$ alkoxy", "protected carboxy", "carboxy protecting group", "protected amino", "amino protecting group", "protected hydroxy", "hydroxy protecting group", and "substituted phenyl" are the same as described for the 4-(R,S)-(substituted selenyl)azetidinone starting materials of the above formula I.

Examples of $R_5$ wherein $R_f$ is (1) an arylalkyl group of the formula:

$R_g$—(O)$_m$—CH$_2$—;

or (2) a substituted arylalkyl group of the formula

(3) a heteroarylmethyl group of the formula $R_2$—CH$_2$— are as discussed above for the corresponding groups of $R_1$ of the starting materials represented by formula I.

The term "$C_1$ to $C_6$ alkyl or cycloalkyl" refers to methyl, ethyl, n-propyl, n-butyl, iso-butyl, pentyl, n-hexyl, cyclobutyl, cyclopentyl, cyclohexyl and the like. The term "phenyl($C_1$ to $C_4$)alkyl" refers to groups such as benzyl, 2-phenethyl, 2-phenyl-n-propyl, 4-phenyl-n-butyl, 1-phenyl-n-butyl, 3-phenyl-iso-butyl and the like.

The term "free radical initiator" refers to those agents known in the art as a ready source of free radicals to initiate free radical chain reaction sequences. For the instant reaction, free radical initiators are either:

(1) a combination of a chemical initiator and heat;

(2) ultraviolet light; or (3) a combination ultraviolet light, heat and a chemical initiator.

The chemical initiators can be any of the broad class of such compounds that generate carbon radicals, such as:

(1) peroxides: this class includes the diacylperoxides such as diacetylperoxide and dibenzoylperoxide, (2) peroxyesters: this class includes compounds such as the t-butyl acetylperoxide; and (3) azo compounds: this class of compounds includes phenylazotriphenylmethane and 2,2'-azo-biz(2-methylpropionitrile) ("AIBN").

In addition to the above chemical initiators, the heat supplied to initiate the reaction should be in the range from between about 40° to about 130° C. This heat is conveniently supplied by refluxing solvents such as benzene (boiling point 80.1° C.), dimethoxyethane (boiling point 85° C.), and toluene (boiling point 110° C.).

The ultraviolet light source used to initiate the reaction can be any commercially available source, preferably those used for photochemical applications.

The term "substantially anhydrous" as used in the present description means that, although anhydrous organic solvents are generally preferred, trace amounts of water, such as that often found in commercially available solvents, can be tolerated. The presence of such trace amounts of water can be compensated for by using additional amounts of the chemical free radical initiator, the allyl tin reagent (IV), and the starting material (II). It is preferred that conventional laboratory techniques be employed to dry the solvents and to exclude moisture from the solvent. For instance, benzene can be distilled to give anhydrous benzene, and dimethoxyethane can be refluxed over sodium or sodiumpotassium alloy then distilled to yield the anhydrous compound.

The term "aromatic hydrocarbon" denotes benzene, toluene, ethylbenzene, cumene, o,m,p-xylene, mesitylene and like compounds.

The term "substantially inert atmosphere" refers to gasses such as nitrogen and argon. It is preferable that the argon or nitrogen be first passed through a drying column before it is used over the reaction mixture.

In the above process of Scheme I it is preferred that an approximately 1 molar solution of the azetidinone (II) be used. The allyl tin reagent (IV) should preferably be present in about 3 molar equivalents per equivalent of starting material (II) used. When the combination of heat and a chemical initiator are used, the preferred temperature for the reaction is from between about 70° C. to about 130° C. The preferred chemical initiators are the azo class of compounds, especially AIBN. It is preferred that only a catalytic amount of the chemical initiator be used, however greater quantities can be used if deemed necessary to progress the reaction. The solvents for the above process are preferably dried before use and are preferably benzene and dimethoxyethane. The order of addition of reagents and starting materials is not critical, but is preferred that the starting material (II) is first dissolved in the solvent, the allyl tin reagent (IV) added, the mixture is heated followed by the addition of the chemical initiator. Alternatively, the last step could be irradiation of the mixture with ultraviolet light. A positive pressure of nitrogen or argon should be maintained throughout the entire reaction so as to exclude moisture and oxygen.

The progress of the instant process can be monitored in a conventional manner, such as by thin layer chromatography, high performance liquid chromatography, or by analyzing small aliquots of the reaction mixture spectorscopically. The instant process is generally complete in from between about 1 to 3 hours, but this figure varies with the type and amount of substrate and reagent, the solvent and the temperature used, among other variables.

The 4-(R,S)-(allyl or substituted allyl)azetidionone compounds (III) produced by the present process can be isolated and purified by conventional laboratory techniques including extraction, crystallization and recrystallization, trituration and chromatography.

An interesting feature of the instant process is the varying amounts of cis and trans isomers at the 3 and 4 positions of the products (III) that are obtained by varying the group at $R_5$. An illustration of the effect of the $R_5$ substituent on the stereochemistry of the product (III) is demonstrated below by the reaction depicted in Table 1.

TABLE 1
Effect of $R_5$ on Stereoselectivity of the Reaction

| $R_5$ | Product ratio (trans:cis) |
|---|---|
| t-butoxycarbonyl | 100:0 |
| benzoyl | 85:15 |
| benzyloxycarbonyl | 50:50 |
| 2-phenylacetyl | 50:50 |
| 2-phenoxyacetyl | 50:50 |
| allyloxycarbonyl | 30:70 |

The variable stereoselectivity at C-3 and C-4 of the products (III) of the process affords an efficient synthesis of 6-aminocarbapenem and monobactam antibiotics. At the positions corresponding to 3 and 4 in the product (III), the desired configuration of these antibiotics is (5R,6S) for the 6-hydrogen carbapenems and (3S,4R) or (3S,4S) for the monobactams. Thus, as the above Table 1 indicates, the instant process offers a stereospecific route to either one of these antibiotics based on the choice of the group at $R_5$.

The perferred starting materials, product and reagent for the process of Scheme I are when:

$R_5$ is a group of the formula

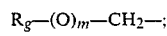

wherein:
(1) $R_f$ is $C_1$ to $C_6$ alkoxy, allyloxy, phenoxy, benzyloxy or 4-methoxybenzyloxy; or
(2) an arylalkyl group of the formula

$R_7$ is hydrogen or (protected carboxy)methyl;
$R_8$ is hydrogen or an amino-protecting group; and
$R_{10}$ is a group of the formula —Se—$R_{11}$ A more preferred group of substitutents among the above preferred group occurs when:
$R_5$ is a group of the formula

wherein:
$R_f$ is
(1) t-butoxy, allyloxy, or benzyloxy; or
(2) an arylalkyl group of the formula $R_g$—(O)$_m$—CH$_2$— wherein
  $R_g$ is phenyl;
  $R_6$ is hydrogen;
  $R_8$ is hydrogen or tri(alkyl)silyl; and
  $R_{11}$ is C$_1$ to C$_4$ alkyl, phenyl, 1-naphthyl or 2-naphthyl.

The most preferred substituents within the above class of more preferred substituents occurs when;
  $R_5$ is a group of the formula

wherein
  $R_f$ is
    (1) t-butoxy; or
    (2) an arylalkyl group of the formula $R_g$—(O)$_m$—CH$_2$— wherein $R_g$ is phenyl and m is one;
  $R_7$ is hydrogen, (methyl carboxylate)methyl or (benzyl carboxylate)methyl;
  $R_8$ is hydrogen, trimethylsilyl, or (t-butyl)dimethylsilyl;
  $R_9$ is n-butyl; and
  $R_{10}$ is a group of the formula —Se—$R_{11}$ wherein $R_{11}$ is methyl or phenyl.

Certain 3-(S)-(acylamino)-4-(S)-(2'-(allyl or substituted)allyl)azetidinone products and the corresponding 3-(R)-3-methoxy-3-acylamino analogs of the above process in Scheme I are the third aspect of this invention. These products are depicted below in formula V:

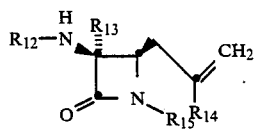

wherein
  $R_{12}$ is an acyl group of the formula

wherein $R_k$ is
  (a) C$_1$ to C$_7$ alkyl, cyanomethyl, 4-protected amino-4-protected carboxybutyl; or
  (b) C$_1$ to C$_6$ alkoxy, allyloxy, phenoxy, benzyloxy or 4-methoxybenzyloxy; or
  (c) the group $R_1$, wherein $R_1$ is phenyl or substituted phenyl, wherein the substituents are one or two halogens, protected hydroxy, cyano, trifluoromethyl, C$_1$ to C$_4$ alkyl, C$_1$ to C$_4$ alkoxy, protected amino, protected carboxy, protected carboxymethyl, protected hydroxymethyl or protected aminomethyl; or
  (d) an arylalkyl group of the formula $R_1$—(O)$_m$—CH$_2$— wherein m is 0 or 1; or
  (e) a substituted arylalkyl group of the formula

wherein $R_m$ is $R_1$ as defined above, thien-2-yl, thien-3-yl, fur-2-yl, fur-3-yl; W is protected hydroxy, protected carboxy, protected amino; or
  (f) a heteroarylmethyl group of the formula $R_n$—CH$_2$— wherein $R_n$ is thien-2-yl, thien-3-yl, fur-2-yl, fur-3-yl, thiazol-2-yl, tetrazol-5-yl, or tetrazol-1-yl;
  $R_{13}$ is hydrogen or methoxy;
  $R_{14}$ is hydrogen, C$_1$ to C$_6$ alkyl or cycloalkyl, phenyl, phenyl(C$_1$ to C$_4$)alkyl or (protected carboxy)methyl; and
  $R_{15}$ is hydrogen or an amino-protecting group.

As used in conjunction with the product compounds of formula V, the terms "C$_1$ to C$_7$ alkyl", "C$_1$ to C$_6$ alkoxy", "substituted phenyl", "C$_1$ to C$_4$ alkyl", "C$_1$ to C$_4$ alkoxy", "protected carboxy", "carboxy protecting group", "protected amino", "amino protecting group", "protected hydroxy", "hydroxy protecting group", "C$_1$ to C$_6$ alkyl or cycloalkyl", and "phenyl(C$_1$ to C$_4$)alkyl" are as described for the compounds represented by formulas II, III and IV in the above Scheme I.

Examples of $R_{12}$ wherein $R_k$ is:
  (1) an arylalkyl group of the formula $R_1$—(O)$_m$—CH$_2$—;

(2) a substituted arylalkyl group of the formula

or
  (3) a heteroarylmethyl group of the formula $R_n$—CH$_2$— are as discussed for the corresponding groups at $R_1$ of the starting materials (I).

The preferred substituents for the above product compounds of formula V are when:
  $R_{12}$ is an acyl group of the formula

wherein $R_k$ is:
  (1) C$_1$ to C$_6$ alkoxy, allyloxy, phenoxy, benzyloxy, or 4-methoxybenzyloxy; or
  (2) an arylalkyl group of the formula
  $R_1$—(O)$_m$—CH$_2$—;

and $R_{14}$ is hydrogen or (protected carboxy)methyl.

A more preferred group of substituents is encompassed within the above group of preferred substituents when:

$R_{12}$ is an acyl group of the formula

wherein $R_k$ is:
(1) t-butoxy, allyloxy, benzyloxy; or
(2) an arylalkyl group of the formula

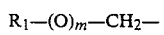

wherein $R_1$ is phenyl;
$R_{13}$ is hydrogen; and
$R_{15}$ is hydrogen or tri(alkyl)silyl.

the most preferred substituents are encompassed within the above group of more preferred substituents when:

$R_{12}$ is an acyl group of the formula

wherein $R_k$ is:
(1) t-butoxy; or
(2) an arylalkyl group of the formula

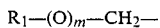

wherein $R_1$ is phenyl and m is 1;
$R_{14}$ is hydrogen, (methyl carboxylate)methyl, or (benzyl carboxylate)methyl; and
$R_{15}$ is hydrogen, tri(methyl)silyl, or (t-butyl)dimethylsilyl.

II.

SYNTHESIS OF STARTING MATERIALS

The synthesis of 4-(R,S)-(chloro, bromo, substituted thio or substituted selenyl)azetidinone starting materials (formula II, Scheme I above) from penicillins and/or cephalosporins is discussed below. Encompassed in this discussion is the synthesis of the 4-(R,S)-(substituted selenyl)azetidinone starting materials represented by the above formula I.

The synthesis of the starting materials will be discussed in two general parts. First, the synthesis of compounds wherein $R_{10}$ is a group of the formula

or

i.e., the 4-(R,S)-(substituted thio and substituted selenyl)azetidinone compounds will be discussed. Second, the synthesis of compounds wherein $R_{10}$ is chloro or bromo, i.e., the 4-(R,S)-(chloro or bromo)azetidinones will be discussed.

A. Synthesis of 4-(R,S)-(substituted thio and substituted selenyl)azetidinone starting materials The synthesis of the 4-(R,S)-(substituted thio and substituted selenyl)azetidinone starting materials is conveniently discussed in 3 parts:

(1) synthesis of 4-(S)-acetoxyazetidinone precursors;
(2) synthesis of starting materials wherein $R_8$ is hydrogen or an amino-protecting group; and
(3) synthesis of starting materials wherein $R_8$ is the seco-penicillin moiety.

The 4-(S)-acetoxy azetidinone precursors, wherein the ring nitrogen is substituted by hydrogen, an amino-protecting group or the seco-penicillin moiety will be discussed as one group. The 4-(R,S)-(substituted thio or substituted selenyl)azetidinone starting materials will be discussed in two parts: (1) wherein the azetidinone ring nitrogen is substituted with hydrogen or amino-protecting group; (2) wherein the ring nitrogen is substituted with a seco-penicillin moiety.

1. Synthesis of 4-(S)-acetoxyazetidinone precursors

The synthesis of 4-(S)-acetoxyazetidinone precursors is outlined below in Diagram A

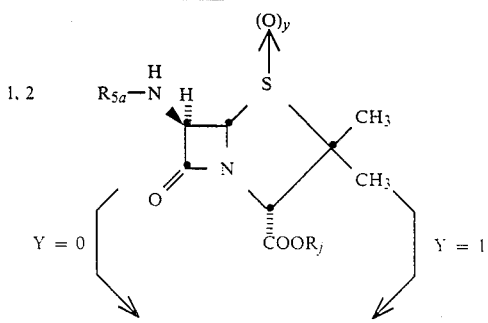

Diagram A

Diagram A

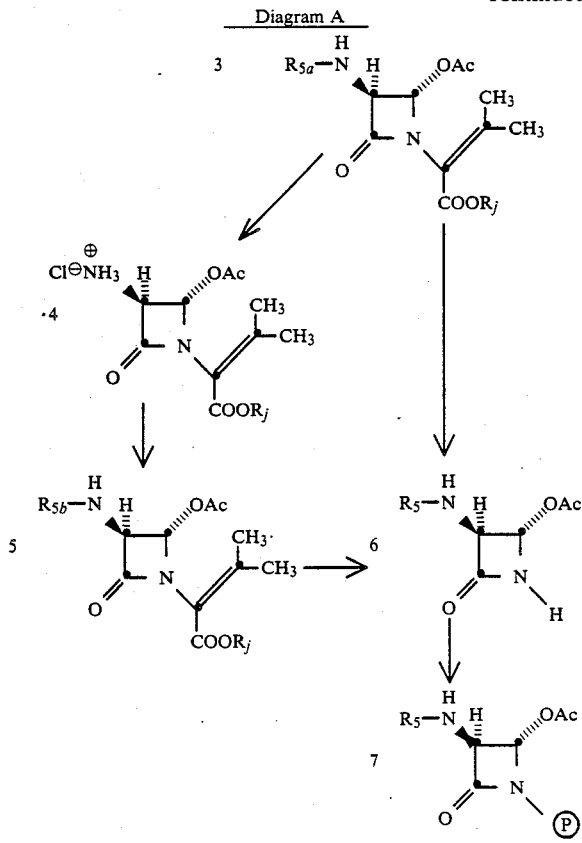

In the above Diagram A, R$_5$, and R$_j$ are the same as for the corresponding numbers of the compounds in the above Scheme I. Y is 0 or 1. R$_{5a}$ is the same as R$_5$ with the deletion from R$_f$ of the groups C$_1$ to C$_6$ alkoxy, allyloxy, phenoxy, benzyloxy and 4-methoxybenzyloxy. R$_{5b}$ is R$_5$ only when R$_f$ is C$_1$ to C$_6$ alkoxy, allyloxy, phenoxy, benzyloxy, or 4-methoxybenzyloxy. Finally, the symbol Ⓟ represents an amino-protecting group as defined for any of the compounds above.

Referring to the above Diagram A, the 5-membered ring of a (5S,6R)-penicillin sulfide (1) or a (5S,6R)-penicillin sulfoxide (2) can be cleaved to give the 4-acetoxyazetidinone (3). Specifically, the penicillin sulfide (1) is treated with an excess of mercuric acetate in a solvent such as acetic acid at 100° C. under an inert atmosphere. The conversion of the sulfide (1) to the 4-acetoxyazetidinone (3) under those conditions can take as little as 15 minutes. The 5-membered ring of the penicillin sulfoxide (2) is cleaved under well known conditions. For instance, under an inert atmosphere, the 4-acetoxyazetidinone (3) is obtained by treating the sulfoxide (2) with trimethylphosphite (2.5 equivalents) and acetic acid (7.5 equivalents) in refluxing toluene.

The 4-acetoxyazetidinone compound (6) can be synthesized by one of two routes. In the first route, the 4-acetoxyazetidinone N-(seco-penicillin) derivative (3) is treated with an equimolar amount of potassium permanganate in an acetone/water solvent at room temperature. The second route involves the intermediate steps of amide side-chain cleavage followed by reacylation with the R$_{5b}$ side chain. The side chain cleavage step involves methods well known in the art. For example, the triphenylphosphite-chlorine-pyridine kinetic complex, described in Bunnel, U.S. Pat. No. 4,223,133 issued Sept. 16, 1980, can be employed. This method entails bubbling chlorine gas through a halogenated hydrocarbon such as methylene chloride at a temperature around −35° C. until a yellow color persists. This color is titrated away by the addition of triphenylphosphite. The substrate (3) is added followed by the addition of sufficient pyridine to complex the newly formed kinetic species. The reaction mixture is stirred at room temperature until completion. The mixture is then cooled to approximately −10° C., hydrogen chloride gas is bubbled through the mixture for short period, followed by the addition of iso-butyl alcohol. This mixture is stirred for approximately 1.5 hours to give the amine hydrochloride salt (4). The amine hydrochloride salt (4) is then acylated with a urethan amino-protecting group using standard methods known in the art. Such methods are described in the Greene and McOmie references listed above under the definitions of an amino-protecting group. For example, the substrate (4) is combined with di-(t-butyl)dicarbonate in tetrahydrofuran followed by the immediate addition of solid sodium bicarbonate. This reaction is stirred at room temperature until completion to give the 3-(S)-t-butoxycarbonylamino compound, a species of the class of 3-(S)-acylated-4-(S)-acetoxyazetidinone N-(seco-penicillin) compounds (5).

The seco-pencillin moiety of the reacylated azetidinone (5) is removed by dissolving the substrate in a 1:1 methylene chloride:methanol solution, cooling the solution to −74° C., and bubbling ozone through the solution until it takes on a bluish tinge. At the end of the addition of the ozone, nitrogen is used to purge the solution. To quench the reaction, dimethylsulfide is added to the solution.

The last reaction depicted above in Diagram A, the conversion of the N-H compound (6) to the N-(protected-amino) compound (7), is carried out by standard methods used for protecting amino groups in the β-lactam art. For instance, the ring nitrogen can be silylated with the tri(methyl)silyl group as follows: the substrate (6) is mixed in methylene chloride with bis((trimethyl)silyl)trifluoroacetamide(5.0 equivalents) under nitrogen. In an alternative procedure, the substrate (6) is added to tetrahydrofuran followed by the addition of triethylamine. This reaction mixture is cooled to 0° C. and tri(methyl)silyl chloride is added. Both of these procedures result in the N-trimethylsilyl compound (7) Ⓟ is trimethylsilyl). In a similar fashion, the ring nitrogen is silylated with the (t-butyl)dimethylsilyl group by dissolving the substrate (6) and (t-butyl)dimethylsilyl chloride in acetonitrile, followed by the addition of triethylamine to the solution.

2. Synthesis of N-H, N-Ⓟ 4-(R,S)-(substituted selenyl or substituted thio)azetidinones The 4-(S)-acetoxyazetidinone precursors substituted at nitrogen with a hydrogen (6) or an amino protecting group (7) in Diagram A are converted to the corresponding 4-(R,S)-(substituted selenyl or substituted thio)azetidinone compounds as outlined in the following Diagram B.

substituted thiol in methylene chloride at low temperature (approximately 0° C.) in an inert atmosphere.

The second route synthesizes the 4-(R,S)-(substituted selenyl) compounds. Selenium metal is first dissolved in tetrahydrofuran. The appropriate alkyl- or aryllithium reagent is added to the solution and the solution is cooled to approximately −50° C. The substrate is added and the reaction is stirred under nitrogen under substantially complete. The reaction is quenched by adding a 2M solution of acetic acid in tetrahydrofuran.

The 4-(S)-acetoxyazetidinone N-H compounds (6) are converted to the 4-(R,S)-(substituted thio or substituted selenyl)azetidinone N-H compound (8) by the second route discussed for the conversion of the corresponding N-Ⓟ azetidinones ((7) to (9)).

The interconversion of the N-H and N-Ⓟ 4-(R,S)-acetoxyazetidinones (6 to 7, 7 to 6) and the N-H and N-Ⓟ 4-(R,S)-(substituted thio or substituted selenyl)azetidinones (8 to 9, 9 to 8) is accomplished by methods well known in the art. For example, the azetidinone ring nitrogen can be protected as discussed above in Diagram A (e.g., 6 to 7). Furthermore, the nitrogen is sometimes deprotected during the workup of the product (9). For example, when P is trimethylsilyl on the 4-(R,S)-(substituted thio or substituted selenyl)azetidinone (9), the compound is deprotected to give the corresponding

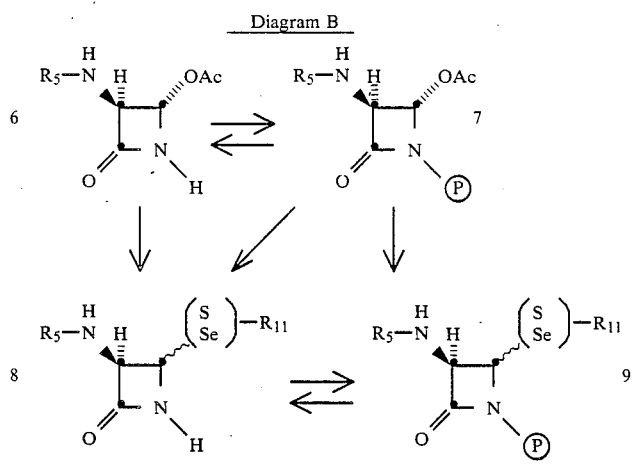

Diagram B

In the above Diagram B, $R_5$, $R_{11}$, and Ⓟ are the same as in the above Diagram A.

The replacement of the acetoxy group in the precursor (7) by a substituted thiol or substituted selenyl group to give the corresponding starting material (9) is accomplished with two general methods. The first method involves reacting the precursor (7) with boron trifluoride-etherate and the appropriate substituted selenol or N-H compound (8) on contact with silica gel or moisture.

3. Synthesis of N-(seco-penicillin)-4-(R,S)-(substituted selenyl)azetidinones

The 4-(S)-acetoxyazetidinones substituted on the azetidinone ring nitrogen with a seco-pencillin moiety (Diagram A, compounds 3 and 5) are converted to the corresponding 4-(R,S)-(substituted selenyl)azetidinones (11) as represented in the following Diagram C.

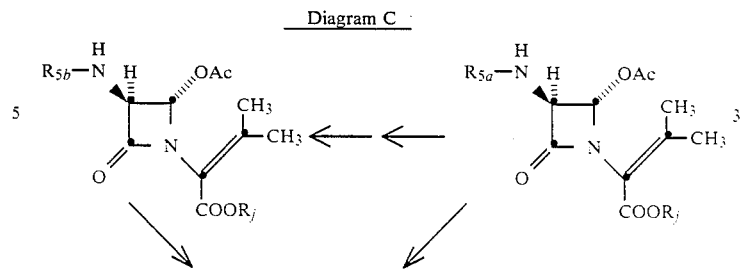

Diagram C

-continued

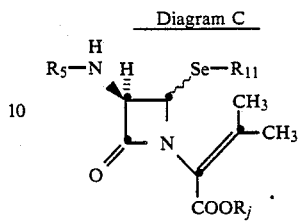

$R_{5a}$, $R_{5b}$, $R_5$, $R_{11}$, and $R_j$ have the same meanings as they do for the terms in Diagram A above. At this point it is useful to recall that $R_{5b}$ stands for $R_f$ when $R_f$ is only $C_1$ to $C_6$ alkoxy, allyloxy, phenoxy, benzyloxy, and 4-methoxybenzyloxy. On the other hand, $R_{5a}$ is $R_f$ when $R_f$ represents everything but $C_1$ to $C_6$ alkoxy, allyloxy, phenoxy, benzyloxy, and 4-methoxybenzyloxy.

In Diagram C, the deacylation/reacylation of (3) to give (5) is carried out identically to the procedure described for these compounds in Diagram A.

The 4-(S)-acetoxyazetidinone precursors (5, 3) are converted to the corresponding 4-(R,S)-(substituted selenyl) azetidinone starting materials (10) by either of the two routes outlined for the conversion of the 4-(S)-acetoxyazetidinone N-Ⓟ compounds (7) to the 4-(R,S)-(substituted selenyl)azetidinone N-Ⓟ compounds (9) in Diagram B above.

B. Synthesis of 4-(R,S)-(Chloro or Bromo)Azetidinone Starting Materials 4-(R,S)-(chloro or bromo)azetidinone starting materials are synthesized from penicillin sulfones and 3-methyl cephalosporin sulfones as outlined in the following Diagram D.

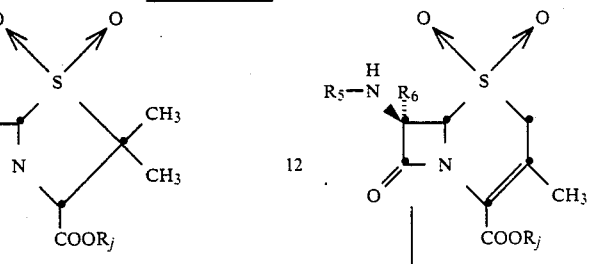

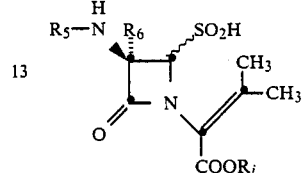

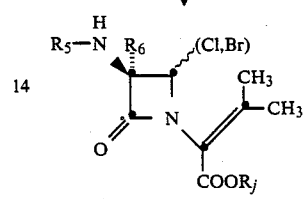

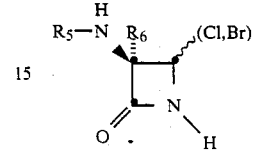

Diagram D

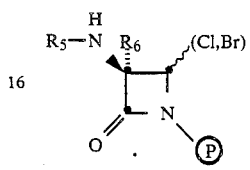

In the above Diagram D, $R_5$, $R_6$, $R_j$, and P have the same meaning as described for Diagrams A, B, and C above. In the specific reactions in Diagram D, the penicillin sulfone (11) is cleaved to the 4-(sulfinic acid)azetidinone (13) with a hindered amine base. The preferred base is 1,8-diazabicyclo[5.4.0]undec-7-ene (DBU). For example, (5R,6S)-6-(phenylacetamido)-6-(methoxy)penicillin-1-sulfone is dissolved in methylene chloride and the solution cooled to 0° C. One equivalent of DBU is added and the mixture is stirred at low temperature for 30 minutes to give the corresponding 4-(sulfinic acid)azetidinone (13).

The 3-methylcephalosporin sulfone (12) is cleaved to the 4-(sulfinic acid)azetidinone (13) with ammonium chloride and zinc. For example, under a nitrogen atmosphere, benzyl (7S,6R)-7-(phenoxyacetamido)-7-methoxy-3-methyl-3-cephem-4-carboxylate sulfone is dissolved in a 10:1 ethanol:methylene chloride solution. Ammonium chloride (18 equivalents) is added and the mixture is stirred at room temperature overnight. This reaction gave a mixture of $\alpha,\beta$ and $\beta,Y$ isomers on the seco-penicillin tail of the azetidinone (13).

The 4-(R,S)-(chloro or bromo)azetidinones (14) are synthesized by reacting the corresponding 4-(sulfinic acid)azetidinones (13) with N-chlorosuccinimide or N-bromosuccinimide, respectively. Additionally, t-butyl hypochlorite or N-chlorophthalimide can be used to make the 4-chloro derivative. For example, a 4-(sulfinic acid)azetidinone (13) (wherein $R_6$ is methoxy, $R_5$ and the nitrogen taken together are phenylacetamido, and $R_j$ is benzyl) is dissolved in methylene chloride, the solution cooled to $-54°$ C. and about 1 equivalent of t-butylhypochlorite is added to the solution. The solution is stirred at low temperature for less than an hour. The reaction is quenched by extracting the solution with a 1N sodium thiosulfate solution.

An example of the bromination procedure entails dissolving a 4-(sulfinic acid)azetidinone (13) (wherein $R_6$ is methoxy, $R_5$ and the nitrogen taken together are phenoxyacetamido and $R_j$ is benzyl) in methylene chloride under nitrogen. The solution cooled to 0° C., N-bromosuccinimide (2 equivalents) is added and the solution is stirred for approximately 1 hour. The reaction is quenched by adding a 1N solution of sodium thiosulfate to the solution.

The N-(seco-penicillin)-4-(R,S)-(chloro or bromo)azetidinone (14) is a suitable substrate for reaction in the process of Scheme I. However, the N-(seco-penicillin) moiety can be removed to give the N-H species (15) as a substrate for the same process. The seco-penicillin moiety can be removed by the ozonolysis/methanolysis procedure or the potassium permanganate/(acetone/water) procedure discussed in the above Diagram A (the conversion of compounds 5 to 6 and 3 to 6, respectively,).

Similarly, the N-H compound is a suitable substrate in the process outlined by Scheme I above, but this compound can be converted to the corresponding N-(amino-protected) compound (16) in a conversion analogous to that described above in Diagram A (6 to 7).

III.

THE PROCESS:SYNTHESIS OF 4-(R,S)-(2-(SUBSTITUTED OR UNSUBSTITUTED)ALLYL)AZETIDINONES WITH 2-(SUBSTITUTED OR UNSUBSTITUTED) ALLYL TIN COMPOUNDS UNDER FREE RADICAL CONDITIONS

The process of the instant invention is depicted generally above in Scheme I. The discussion of the process is divided in parts based on the substituents on the azetidinone ring nitrogen of the starting materials and the products.

In one part of the process, the substituent on the azetidinone nitrogen ($R_8$) is hydrogen or an amino-protecting group. This part of the process is represented below in Diagram E.

Diagram E

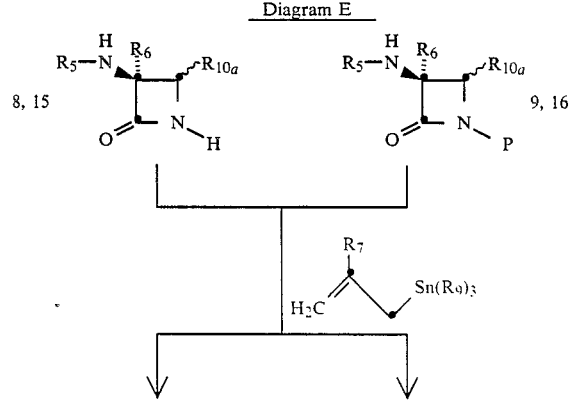

Diagram E

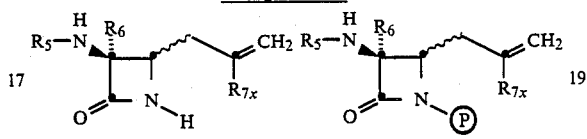

and

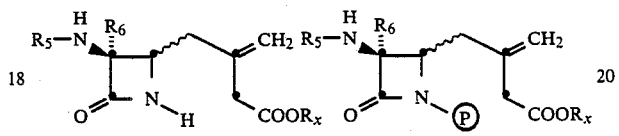

In the above Diagram E, $R_5$, $R_6$, $R_7$, $R_9$, and (P) have the same meaning as defined for them in the above Scheme I. $R_{10a}$ is the same as $R_{10}$ above. (Note, however, that when $R_6$ is methoxy, $R_{10a}$ is other than substituted selenyl or substituted thio.) $R_{7x}$ encompasses all of the groups defined by $R_7$ except for the (protected carboxy)methyl group. $R_x$ represents a carboxy protecting group as defined at numerous places above.

The 4-(R,S)-(substituted thio and substituted selenyl)azetidinone starting materials (8, 9) in the above Diagram E are synthesized according to the scheme of Diagram B. The 4-(R,S)-(chloro or bromo)azetidinones starting materials (15, 16) are synthesized according to the route outlined in the above Diagram D.

Note in the above Diagram E that the products are arbitrarly divided based on the differences in the substituent $R_7$. Thus, there is a class of products wherein $R_7$ is (protected carboxy)methyl (18, 20) and a class where $R_7$ is $R_{7x}$, i.e., all of the groups encompassed by $R_7$ except the (protected carboxy)methyl group. The process described in Diagram E produces the products represented by formula V above.

The second part of the process employs starting materials wherein the azetidinone ring nitrogen is substituted with the seco-penicillin moiety. This synthetic scheme is depicted below in Diagram F.

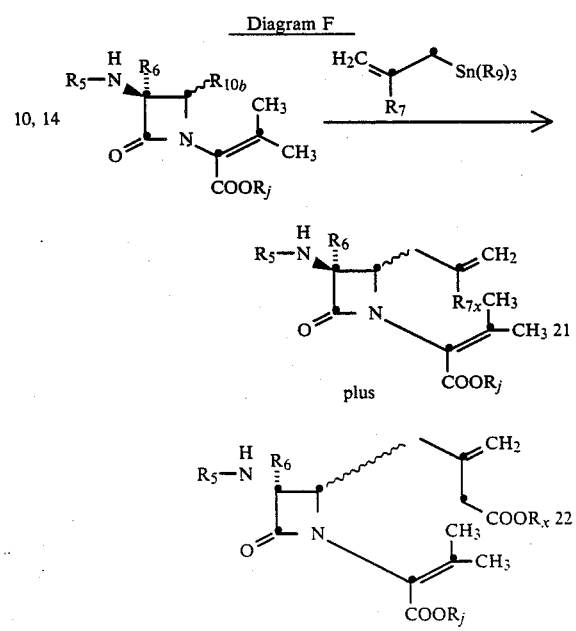

In the above Diagram F, $R_5$, $R_6$, $R_7$, $R_9$, $R_j$, $R_7$ and $R_x$ have the same meanings as defined them for in Diagram E. $R_{10b}$ stands for chloro, bromo, or, when $R_6$ is other than methoxy, a group of the formula $$-Se-R_{11}$$

The starting materials in Diagram F are the 4-(R,S)-(substituted selenyl)azetidinones (10) of Diagram C and the 4-(R,S)-(chloro or bromo) azetidinones (14) of Diagram D.

In Diagram F, an arbitrary distinction is drawn among the products based on differences of $R_7$. As with Diagram E, the products are divided into two groups based on differences in $R_7$: wherein $R_7$ is a (protected carboxy)methyl group (22) and where it is everything that $R_7$ can be but a (protected carboxy)methyl group ($R_{7x}$, 21).

The reaction conditions for Diagrams E and F are discussed above in conjunction with Scheme I.

Compound IV of Scheme I, with "2-(substituted or unsubstituted) allyl tin reagent", or simply the "tin reagent", can be synthesized in one of two ways.

In the first method bis-(trialkyl or triaryl)tin oxide and a 2-(substituted or unsubstituted)allyl Grignard reagent are reacted. This reaction is depicted generally below in Diagram G:

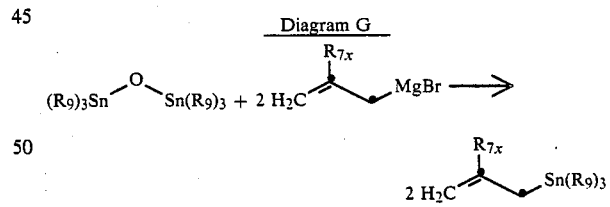

In the above Diagram G, $R_9$ is the same as defined for Scheme I. $R_{7x}$ is the same as defined for Diagram F except that it does not include the (protected carboxy)methyl group.

The conditions of the reaction in Diagram G usually involve generating the Grignard reagent in situ. Under a nitrogen atmosphere, magnesium metal is placed in diethyl ether and activated with iodine. The 2-(unsubstituted or substituted)allyl bromide is added and the mixture is refluxed for about 0.5 hours to about 1.5 hours. Bis(trialkyl or triaryl tin)oxide (0.5 equivalents per equivalent of Grignard reagent present) is added and the solution is refluxed for approximately 1 hour.

The second (and more general) method reacts a (trialkyl or triaryl)tin hydride with a 2-(substituted or unsubstituted)-3-(alkyl or aryl substituted sulfide, sulfoxide, or sulfone) allyl moiety. This reaction is outlined below in Diagram I.

Diagram I

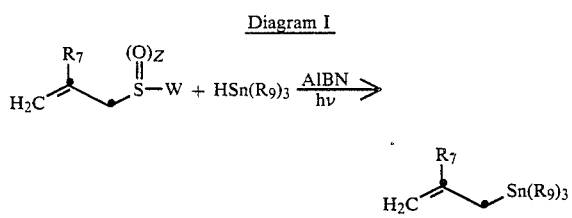

In the above Diagram I, $R_7$ and $R_9$ are as defined above for Scheme I. Z is equal to 0, 1 or 2 and W is phenyl or $C_1$ to $C_6$ alkyl.

The reaction of Diagram I generally is run under an inert atmosphere in an aromatic hydrocarbon solvent such as toluene. The (trialkyl or triaryl)tin hydride and the allyl moiety are combined in the solvent and the reaction is initiated by a chemical initiator such as AIBN and by a U.V. light source.

IV.

SYNTHETIC USES FOR THE PRODUCTS OF THE PROCESS

A. Introduction

The products of the process of Scheme I, represented by compound III, can be converted to members of two distinct classes of antibiotic compounds:

(1) The carbapenems, and specifically the carbapenems of formula VI

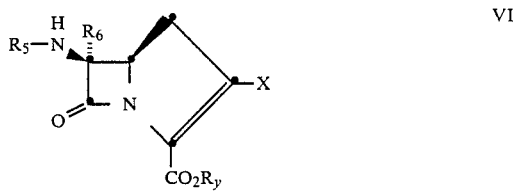

In the above formula VI, $R_5$ and $R_6$ are as defined in Scheme I, $R_y$ is a carboxy protecting group, hydrogen or a pharmaceutically acceptable carboxylic acid salt and X is a wide variety of carbon, sulfur and oxygen substituents, specifically the acetoxy group.

(2) The monobactams, specifically monobactams of the formula VII

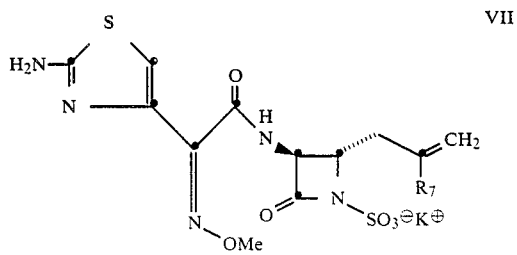

In the above formula VII, $R_7$ is as defined in Scheme I.

B. Synthesis of carbapenems

The synthesis of carbapenems (formula VI) is carried out with the products of the process in Scheme I (17 through 20, Diagram E and 21 and 22, Diagram F, collectively referred to in this section as "products") when $R_7$ (the allyl substituent) on the products is either hydrogen or the (protected carboxy)methyl group. Specifically, compounds 18, 20, and 22 ($R_7$ is (protected carboxy)methyl only) and compound 17, 19, and 21 ($R_{7x}$ is hydrogen only) are useful in the synthesis of carbapenems (referred to in this section as "final products").

The synthesis of carbapenems is discussed in three Routes, with two of these Routes being further divided into Subroutes. The Routes and the Subroutes are based on the differences in the products (17 through 22) and in one case differences in the carbapenem final product. The differences in the products (and final products) are used in the following hierarchy to classify the Routes and Subroutes:

(1) differences at $R_8$: i.e., the substituent on the azetidinone ring nitrogen of the product;

(2) differences at $R_7$: i.e., the substituent on the allyl group of the product;

(3) differences at $R_6$: i.e., the substituent at the C-3 of the azetidinone product and the C-6 position of the carbapenem final product.

The distinctions of the azetidinone products at $R_8$ yields two broad classes of synthetic Routes:

(1) Routes wherein $R_8$ is hydrogen or an amino protecting group;

(2) Routes wherein $R_8$ is a seco-penicillin moiety.

Routes 1 and 2 are encompassed in the first class of synthetic Routes. Thus, Routes 1 and 2 begin with product compounds 17 through 20, Diagram E. Route 3 composes the second class of synthetic routes. Route 3 begins with product compounds 21 and 22 of Diagram F.

The second level of distinction in the hierarchy, i.e. the differences in the products of $R_7$, divides the above first broad class ($R_8$ is hydrogen or an amino protecting group) into Routes 1 and 2. In Route 1, $R_7$ is a (protected carboxy)methyl moiety, and therefore begins with the product compounds 18 and 20. In Route 2, $R_7$ is hydrogen, and therefore begins with compounds 17A and 19A from Diagram E (the "A" denotes that $R_{7x}$ is limited to hydrogen).

The differences in the substituents of the product compounds at $R_7$ divides Route 3 into two Subroutes:

(1) Subroute 3A: wherein $R_7$ is (protected carboxy)methyl and thus starts from compound 22;

(2) Subroute 3B: wherein $R_7$ is hydrogen and thus starts from compound 21A (the "A" denotes that $R_{7x}$ in 21 is limited to hydrogen).

The third level of distinction (distinguishing the products based on the substituent at $R_6$) bears only on Route 2 and the divisions based on this level will be part of the specific discussion of that Route.

(1) Route 1: Starting Materials 18 and 20 of Diagram E ($R_7$ is (protected carboxy)methyl)

Synthetic Route 1 affords both 6-(S)-hydrogen and 6-(R)-methoxy carbapenems. Route 1 employs starting materials with the allyl group at C-4 of the azetidinone moiety substituted with (protected carboxy)methyl (18 and 20, Diagram E). This reaction sequence is outlined below in Diagram J:

Route 1             Diagram J

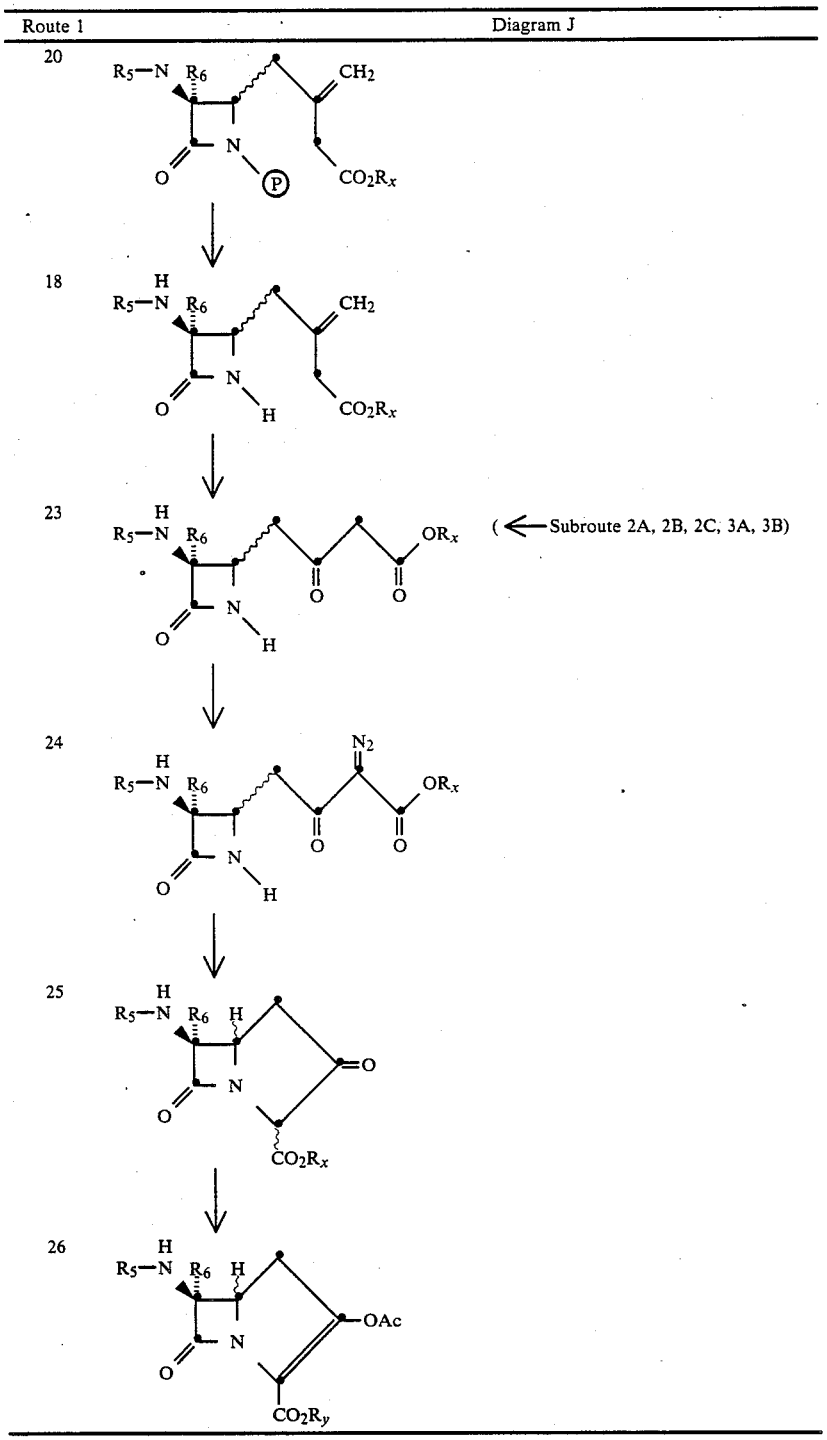

In the above Diagram J, $R_5$ and $R_6$ are as defined above for Scheme I. $R_x$ is a carboxy protecting group as defined above. ⓟ indicates an amino protecting group as defined above. $R_y$ is a carboxy protecting group, hydrogen or a pharmaceutically-acceptable carboxylic acid salt.

In the individual reactions in Diagram J, the conversion of the amino-protected 4-(R,S)-(2-((protected carboxy)methyl)allyl)azetidinone (20) to the corresponding N-H compound (18) is accomplished with the standard amino-protecting group removal conditions. Such conditions are outlined in references such as McOmie and T. W. Greene, discussed above in conjunction with the definition of amino-protecting groups.

The 4-(R,S)-(2-((protected carboxy)methyl)allyl-)azetidinone (18) is ozonized to the 4-(R,S)-($\beta$-ketoester)azetidinone (23) under nitrogen in a 1:1 methanol:methylene chloride solution at low temperature (e.g. $-78°$ C.). After the starting material (18) has been added to the methanol:methylene chloride mixture and the mixture cooled, ozone is bubbled through the mixture until a blueish tinge results. The mixture is purged with nitrogen, warmed to room temperature then quenched with dimethylsulfide.

The 4-(R,S)-(β-ketoester)azetidinone (23) is then subjected to standard diazo transfer reaction conditions to give the 4-(R,S)-(β-ketoester diazo)azetidinone (24). These conditions entail dissolving a substrate (23) in a polar aprotic solvent, such as acetonitrile, under nitrogen. Para-carboxyphenylsulfonazide is then added, followed by the addition of an amine base such as triethylamine. The mixture is stirred at room temperature until the reaction is complete.

The 4-(R,S)-(β-ketoester diazo)azetidinone (24) is a precursor to an annelation process using a diazo insertion reaction. The reaction yields in a 3-ketocarbapenam (25). More specifically, under nitrogen a catalytic amount of the rhodium diacetate dimer is dissolved in benzene and the mixture is refluxed. The substrate (24) is added and the resultant mixture is refluxed for 1 hour then stirred at room temperature for 2 days.

The 3-ketocarbapenam (25) is converted to the corresponding 3-acetoxycarbapenem (26) by acylating the 3-enolate form of 25. For instance, under argon the substrate (25) is dissolved in methylene chloride and the solution cooled to low temperature (e.g. 0° C.). Acetyl chloride (1 equivalent) and pyridine are sequentially added and the reaction mixture is stirred at low temperature (0° C.) for 1.5 hours then at room temperature for 1.5 hours to effect the acylation.

(2) Route 2: Starting materials 17, 19 of Diagram E ($R_7$ is hydrogen)

Route 2 starts with the compounds of Diagram E (17, 19) wherein $R_8$ is an amino-protecting group or hydrogen, and $R_7$ is hydrogen. A further distinction made in Route 2 is based on the presence or absence of a 6-(R)-methoxy group in the carbapenem final products. Final products with a 6-(S)-hydrogen group, are synthesized in the approach in "Subroute 2C". Final products with a 6-(R)-methoxy group are synthesized according to "Subroute 2A" and "Subroute 2B". In Subroute 2A the 6-(R)-methoxy group was not present on starting materials 19A and 17A. Thus, Subroute 2A is also called the "late methoxylation" route. By contrast, in Subroute 2B the requisite methoxy group was present on the starting materials. Thus, Subroute 2B is also called the "early methoxylation" route.

All of the Subroutes of Route 2 converge to give a 4-(R,S)-β-ketoester)azetidinone (23) of Route 1. In Route 1, the 4-(R,S)-(β-ketoester)azetidinone (23) is taken on to 6-(S)-hydrogen- or 6-(R)-methoxycarbapenems (26, Diagram J).

(a) Route 2: Common Intermediates

All 3 Subroutes of Route 2 have common intermediates 27, 29, 28 and 30, and all the Subroutes start from 28 and 30. The synthesis of these common intermediates is outlined below in Diagram K.

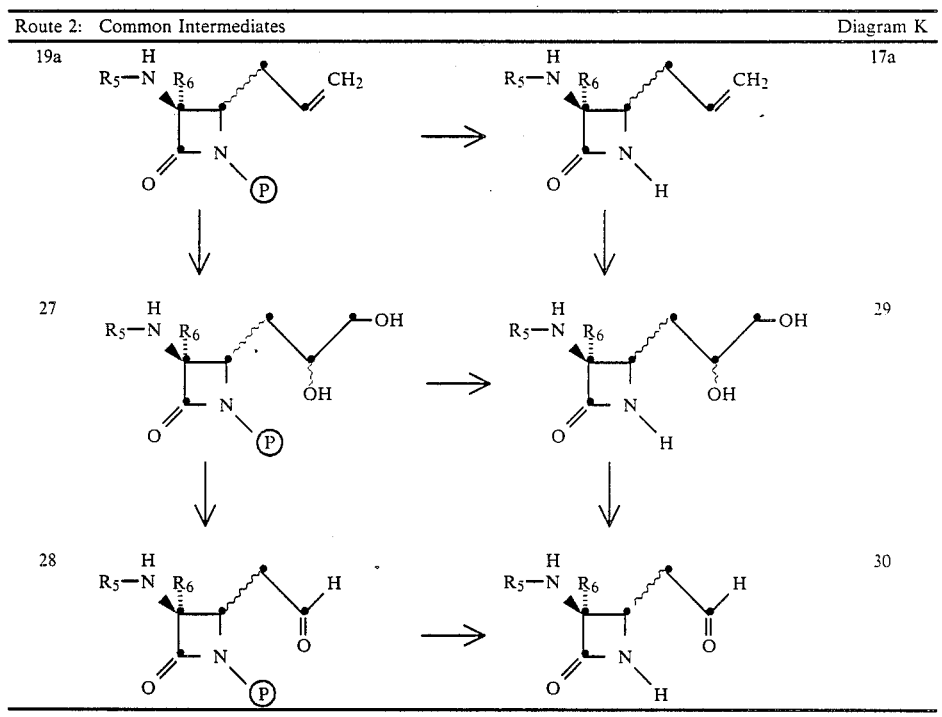

In the above Diagram K, $R_5$, $R_6$ and Ⓟ are as defined in Route 1, Diagram J.

Referring to the specific reactions in Diagram K, the amino-protected 4-(R,S)-(allyl)azetidinone (19A) is oxidized with osmium tetroxide to the corresponding 4-(R,S)-(1',2'-dihydroxyprop-3'-yl)azetidinone (27). The reaction proceeds under a nitrogen atmosphere wherein 4-methylmorpholine-4-oxide is dissolved in deionized water:acetone (2:1) and a t-butanol solution of osmium tetroxide is added. The substrate is added and the reaction mixture is stirred at room temperature until the reaction is substantially complete.

The amino-protected 4-(R,S)-(1',2'-dihydroxyprop-3'-yl)azetidinone (27) is converted to the N-protected 4-(R,S)-(1'-oxoeth-2'-yl)azetidinone (28) with an oxidative loss of carbon. The starting material (27) is dissolved in an aromatic hydrocarbon, such as benzene, under nitrogen. An excess of lead tetraacetate (e.g., 1.5 equivalents) is added and the reaction solution is stirred at room temperature until substantially complete (approximately 1.5 hours).

The conditions outlined above for the amino-protected compounds (19A, 27 and 28) also apply to the corresponding N-H compounds (17A, 29 and 30). The removal of the amino-protecting groups to give the analogous N-H compounds occurs under standard amino-protecting group removal conditions.

(b) Subroute 2A: Late Placement of the Methoxy Group for 6-(R)-methoxycarbapenems Subroute 2A starts with common intermediates 28A and 30A (Diagram K). The "A" following the compound numbers indicates $R_6$ is hydrogen in these products. In this Subroute the hydrogen at $R_6$ is converted to a 3-(R)-methoxy group prior to the ring closure to the carbapenems.

Subroute 2A is outlined below in Diagram L:

| Subroute 2A | Diagram L |

30a, 28a, 31, 32a, 33, 34, 35

Subroute 2A                                    Diagram L

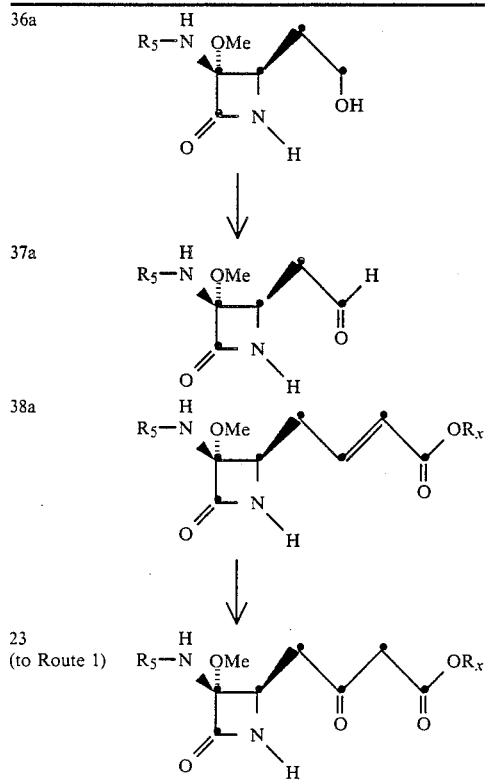

36a
37a
38a
23 (to Route 1)

In the above Diagram L, R₅, ⓟ, and Rₓ are as defined with Route 1, Diagram J.

With regard to the individual reactions of Diagram L, the amino-protected 4-(R,S)-(1-oxoeth-2'-yl)azetidinone (28A) is reduced with sodium borohydride to give amino-protected 4-(R,S)-(1'-hydroxyeth-2'-yl)azetidinone (32A). The reaction is carried out under a nitrogen atmosphere in a polar solvent such as methanol. The substrate is dissolved in methanol and the solution is cooled to a low temperature (e.g. 0° C.). Sodium borohydride is added and the solution is stirred at the low temperature until essentially complete (e.g., 11 minutes) then the reaction quenched with acetone.

This same sodium borohydride reduction is used to convert the corresponding N-H compounds 30A to 31.

The removal of the amino-protecting groups from compounds 28A and 32A to give the corresponding N-H compounds 30A and 31 proceeds with standard methods for removal of amino-protecting groups.

4-(R,S)-(1'-hydroxyeth-2'-yl)azetidinone (31) undergoes protective ring formation to give the 6-(R,S) bicyclo protected species (33). This reaction is conveniently carried out by heating the substrate (31) with 2,2-dimethoxypropane in the presence of a catalyst such as boron trifluoride etherate, toluene sulfonic acid, or the like in a solvent such as methylene chloride, ether, chloroform, dioxane or the like at a temperature from −10° to 35° C. from a few minutes to 1 hour.

The epimers of the diastereomeric mixture of 6-(R,S) bicyclo protected species (33) are separated by chromatography on silica gel using 2:1 ethyl acetate:benzene so that the 6-(S) bicyclo protected species (34) is isolated.

The methoxylation of 6-(S) bicyclo protected species (34) gives the 7-(R)-methoxy-6-(R)-bicyclo protected species (35). Specifically, one equivalent of lithium methoxide is dissolved in a 4:1 mixture of tetrahydrofuran:methanol. The solution is cooled to approximately −72° C. with a dry ice/acetone bath. The substrate (34) then t-butyl hypochlorite are added and the solution is stirred at −70° C. until substantially complete (e.g. 30 minutes). Acetic acid is added to quench the reaction and this mixture is stirred at −70° C. The solution is neutralized with sodium bicarbonate solution and the product (35) is isolated by standard methods.

The protective ring structure is removed from 7-(R)-methoxy bicyclo protected species (35) to give 3-(R)-methoxy-4-(R)-(1'-hydroxyeth-2'-yl)azetidinone (36A). The deblocking reaction is typically conducted by acid hydrolysis. For example, the substrate (35) is treated with aqueous trifluoroacetic acid at a temperature of from 0° to 25° C. for from 5 minutes to 3 hours.

3-(R)-methoxy-4-(R)-(1'-hydroxyeth-2'-yl)azetidinone (36A) is oxidized to give 3-(R)-methoxy-4-(R)-(1'-oxoeth-2'-yl)azetidinone (37A). This aldehyde intermediate (37A) is prepared by treating (36A) with an oxidizing agent such as chromium trioxide·2 pyridine in methylene chloride; a 1:1 mixture of dimethylsulfoxide and acetic anhydride; pyridinium chlorochromate in methylene chloride; or dicyclohexacarbodiimide in dimethylsulfoxide, methylene chloride or the like at a temperature of from about 0° to about 25° C. for from about 5 minutes to 8 hours.

The 3-(R)-methoxy-4-(R)-(1'-oxoeth-2'-yl)azetidinone (37A) is converted to 3-(R)-methoxy-4-(R)-(trans t-butyl but-2'-en-4'-yloate)azetidinone (38A) using the Horner-Emmons modification of the Wittig reaction. For example, sodium hydride is suspended in an aprotic polar solvent, preferably an ether such as dry tetrahydrofuran. The suspension is cooled to 0° C. or below and t-butyl 2-(dimethylphosphonato)acetate is slowly added. This mixture is stirred at low temperature (e.g. 0° C.) until hydrogen evolution ceases. The mixture is then stirred briefly at room temperature, cooled to −20° C. or below and the substrate (37A) is added. The mixture is stirred at −20° C. or below until the reaction is substantially complete.

3-(R)-methoxy-4-(R)-($\beta$-ketoester)azetidinone (23) is obtained from the 3-(R)-methoxy-4-(R)-(trans t-butyl but-2'-en-4'-yloate)azetidinone (38A) by oxypalladation. Sodium tetrachloropalladate and an excess of t-butyl hydroperoxide are dissolved in an aqueous acidic solvent such as 50% aqueous acetic acid. The substrate (38A) is added and the reaction mixture is heated (e.g. 50° C.) until it is substantially complete (e.g. 10 hours). Compound 23 is taken on to a 3-acetoxycarbapenem by the reactions described for Route 1, Diagram J, above.

c. Route 2, Subroute 2B: Early Placement of the Methoxy Group for 6-(R)-methoxycarbapenems In contrast with Subroute 2A, Subroute 2B begins with compounds wherein the C-3 methoxy group is already in place. As such, Subroute 2B begins with common intermediates 30B, Diagram K. (The "B" signifies that $R_6$ on these compounds is methoxy). Thus, in Subroute 2B the methoxylation procedure and the concommitant formation of the ring-protected species is unnecessary. The reaction sequence for Subroute 2B is outlined below in Diagram M:

cussed below. The same conditions apply to the conversions of the amino-protected analogs (28B to 39A to 40A to 23). The amino-protected analogs can be converted to the corresponding N-H compounds by removal of the amino-protecting groups by standard techniques.

The 3-(R)-methoxy-4-(R,S)-(1'-oxoeth-2'-yl)azetidinone (30B) is converted to the corresponding 3-(R)-methoxy-4-(R,S)-(trans t-butyl but-2'-en-4'-yloate)azetidinone (38B) by means of the Horner-Emmons modification of the Wittig reaction. The substrate (30B) is treated with the sodium salt of the t-butyl 2-(dimethylphosphonato)acetate ylid and in a procedure analogous to the conversion of compound 37A to 38A in Subroute 2A, Diagram L.

The 4-(R,S)-($\beta$-ketoester)azetidinone (23) is obtained from the 3-(R)-methoxy-4-(R,S)-(trans t-butyl but-2'-en-4'-yloate)azetidinone (38B) by the oxypallidation method described for the conversion of compound 38A to compound 23 in Subroute 2A, Diagram L above. The 4-(R,S)-($\beta$-ketoester)azetidinone thus produced (23) is an intermediate in the synthesis of 3-acetoxycarbapenems outlined in Route 1, Diagram J above.

d. Subroute 2C: 6-(S)-hydrogen carbapenems

Subroute 2C produces 6-(S)-hydrogen carbapenems (i.e., $R_6$ is hydrogen) from starting materials 30A and 28A. 30A and 28A are species of compound 30 and 28 (Diagram K), wherein $R_6$ is hydrogen only. The 6-(S)-hydrogen carbapenems of Subroute 2C are made in a

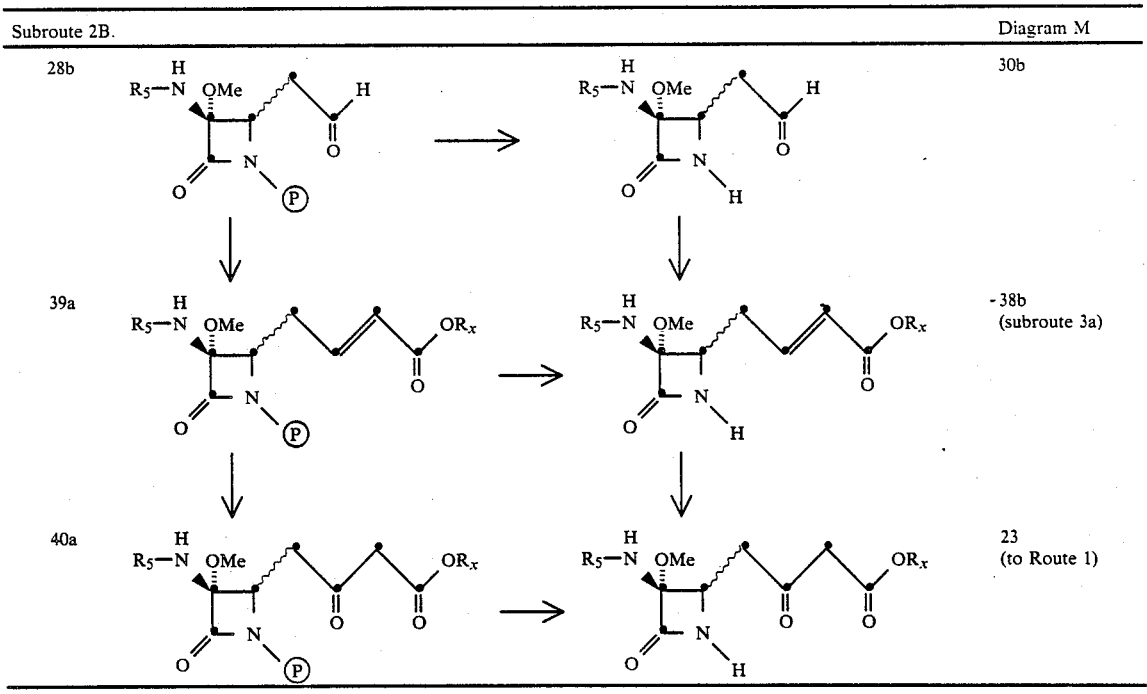

In the above Diagram M, $R_5$, $R_x$ and are as defined above for Route 1, Diagram J.

Referring to the above Diagram M, the reactions for the N-H compounds (30B to 38B to 23) will be dissimilar manner to the 6-(R)-methoxycarbapenems of Subroute 2B. The reaction sequence for Subroute 2C is outlined generally in the following Diagram N:

Structure 2C                                                     Diagram N

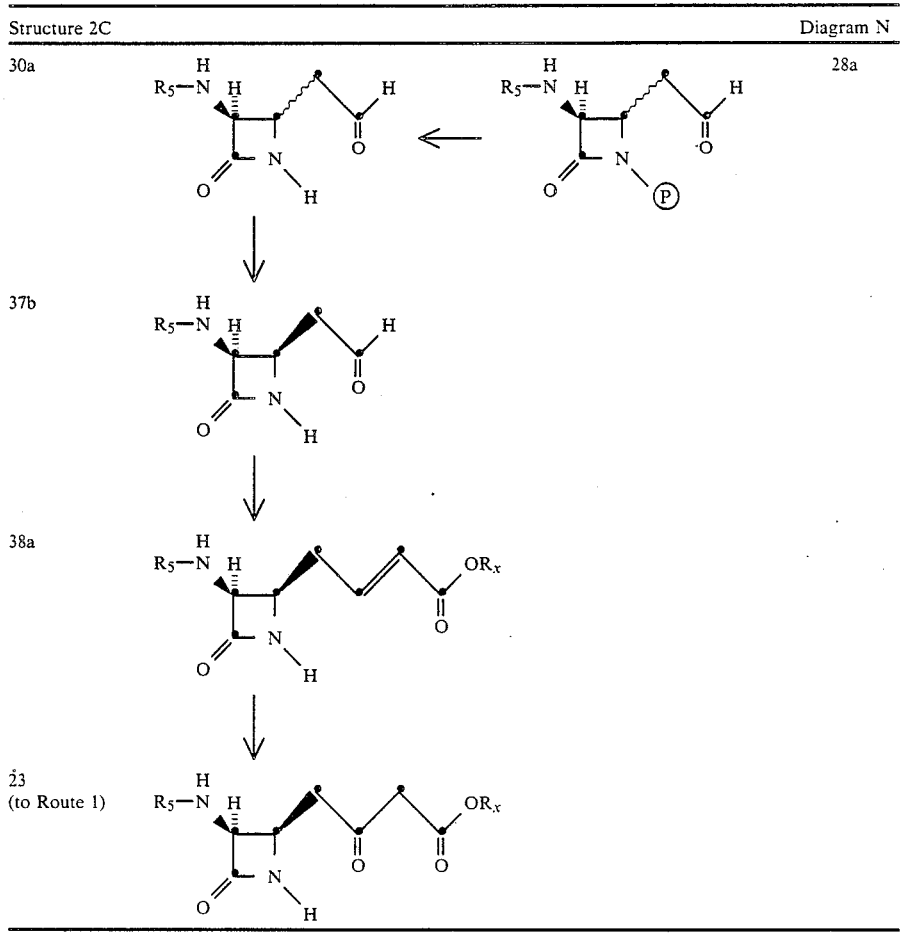

In the above Diagram N, R₅, Rₓ and ⓟ are as defined for Route 1, Diagram J.

The amino-protected 4-(R,S)-(1'-oxoeth-2'-yl)azetidinone (28A) is converted to the corresponding free amine compound (30A) by standard methods for removing amino-protecting groups.

The diasteremoers of the 4-(R,S)-(1'-oxoeth-2'-yl)azetidinone mixture are separated by standard chromatography techniques (such as chromatography of Activity III silica gel, eluting with a gradient of toluene to 80% ethyl acetate/toluene). The 3-(S)-4-(R)-(1'-oxoeth-2'-yl)azetidinone (cis) diastereomer (37B) is isolated and is converted to the 3-(S)-4-(R)-(trans t-butyl but-2'-en-4'-yloate)azetidinone (38A) using the Horner-Emmons modification of the Wittig reaction. This modification reacts t-butyl 2-(dimethylphosphonato)acetate ylid with the substrate (37B) in a manner analogous to the conversion of compound 37A to compound 38A of Subroute 2A, Diagram L.

The 3-(S)-4-(R)-(β-ketoester)azetidinone (23) is obtained from the 3-(S)-4-(R)-(trans t-butyl but-2'-en-4'-yloate)azetindinone (38A) by the oxypallidation procedure described for the conversion of compound 38A to compound 23 in Subroute 2A, Diagram L above.

The 3-(S)-4-(R)-(βketoester)azetidinone (23) is taken on to 6-(S)-hydrogen carbapenems according to the synthesis described in Route 1, Diagram J above.

(3) Route 3: Starting Materials 21 and 22 of Diagram F

Synthetic Route 3 affords carbapenems wherein R₆ is hydrogen and methoxy. Route 3 employs starting materials with a N-seco-penicillin moiety.

Synthetic Route 3 will be discussed in three parts:
(1) the intermediates of Route 3;
(2) Subroute 3A, wherein R₇ is (protected carboxy)methyl;
(3) Subroute 3B, wherein R₇ is hydrogen.

(a) Route-3: Intermediates

The intermediates of Subroute 3A and 3B are discussed together below. These intermediates are analogs that differ only at the R₇ substituent, which is either hydrogen or (protected carboxy)methyl. The synthesis of the intermediates is outlined below in Diagram O:

Route 3 Common Intermediates        Diagram O

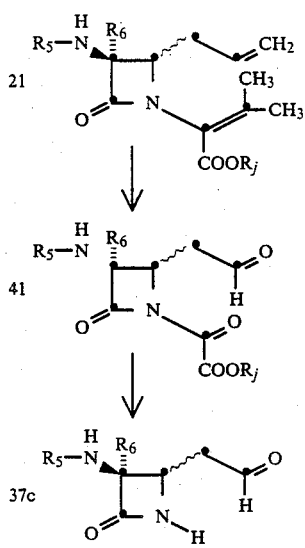
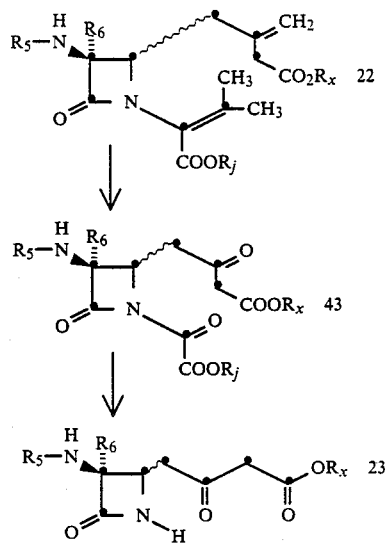

In the above Diagram O, $R_5$, $R_6$ and $R_x$ are the same as defined for Route 1, Diagram J. $R_j$ is the same as described for that symbol in Scheme I.

The following discussion describes the conversion of the intermediates where $R_7$ is hydrogen (21 to 41 to 37C). The same conditions apply to the conversion of the analogs wherein $R_7$ is (protected carboxy)methyl (22 to 43 to 23).

N-(seco-penicillin)-4-(R,S)-(allyl)azetidinone (21) is converted sequentially to the N-glyoxamido-4-(R,S)-(1'-oxoeth-2'-yl)azetidinone (41) then to the free amine 4-(R,S)-(1'-oxoeth-2'-yl)azetidinone (37C) in a one pot, ozonolysis/methanolysis procedure. The substrate (21) is dissolved under nitrogen in a 1:1 methanol/melthylene chloride solution. The solution is cooled to very low temperature (approximately −74° C.) and ozone is bubbled through the solution until a blueish tinge results (approximately 20 minutes to 1 hour). The mixture is purged with a nitrogen flow and the reaction is quenched by the addition of dimethylsulfide.

(b) Subroute 3A: $R_7$ is (protected carboxy)methyl

The 4-(R,S)-(β-ketoester)azetidinone compounds (23), produced as an intermediate in the above Diagram O, are depicted below in Diagram P:

Subroute 3A                                      Diagram P

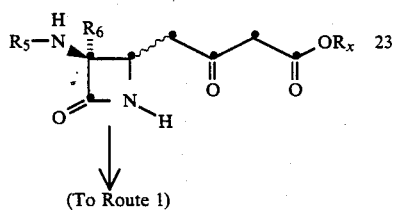

Compound 23 is part of Route 1, Diagram J above. Route 1 converts compound 23 to a carbapenem antibiotic.

(c) Subroute 3B: $R_7$ is hydrogen

The goal of Subroute 3B is to obtain the (β-ketoester)azetidinone (23) of Subroute 3A (Diagram P) and Route 1 (Diagram J). The reaction sequence converting starting material 37C to compound 23, wherein $R_7$ is hydrogen, is outlined below in Diagram Q:

Subroute 3B                                      Diagram Q

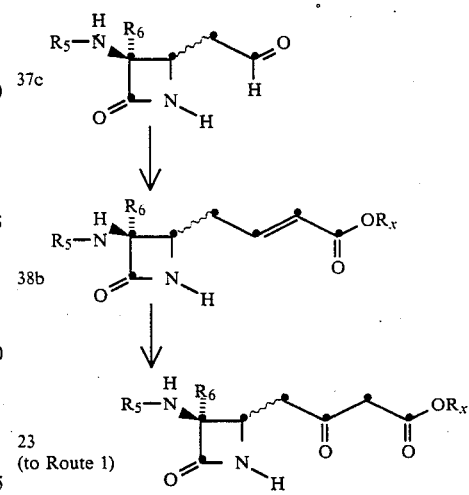

In the above Diagram Q, $R_5$, $R_6$ and $R_x$ are as defined for Route 1, Diagram J.

4-(R,S)-(1'-oxoeth-2'-yl)azetidinone (37C) is reacted with t-butyl 2-(dimethylphosphonato)acetate ylid to give 4-(R,S)-(trans t-butyl but-2'-en-4'-yloate)azetidinone (38B). The reaction conditions for this reaction are the Horner-Emmons modification of the Wittig procedure described for the conversion of 37A to 38A of Subroute 2A, Diagram L.

4-(R,S)-(trans t-butyl but-2'-en-4'-yloate)azetidinone undergoes oxypallidation to give the 4-(R,S)-(β-ketoester)azetidinone (23). The oxypalladation procedure used is analogous to the one for the conversion of compound 38A to 23 in Subroute 2A, Diagram L.

The 4-(R,S)-(β-ketoester)azetidinone (23) is part of Route 1, Diagram J. The reactions associated with Route 1 take compound 23 to a 3-acetoxycarbapenem.

(c) Synthesis of monombactams

The synthesis of monobactam compounds (VII) proceeds from the products of the process in Scheme I wherein $R_6$ is hydrogen. Specifically, product compound 21C of Diagram F ($R_6$ is hydrogen) is the beginning of the monobactam synthesis. Compound 21C is eventually converted to product compound 19C (Diagram E, $R_6$ is hydrogen) prior to the synthesis of a monobactam. Alternatively, the synthesis can start with compound 17C (Diagram E, $R_6$ is hydrogen), which is converted to 19C.

For convenience sake, the discussion of the synthesis of monobactams will be divided into two parts:
(1) monobactams: precursors; and
(2) monobactams: final products.

(1) Monobactams: Precursors

The "precursors" to monobactam-like compounds all are substituted on the 3-(S) nitrogen with the $R_{5a}$ group. This group is the same as $R_5$ except that $R_f$ is not $C_1$ to $C_6$ alkoxy, allyloxy, phenoxy, benzyloxy and 4-methoxybenzyloxy. The synthesis of the precursors is outlined below in Diagram R:

Monobactam Precursors                    Diagram R

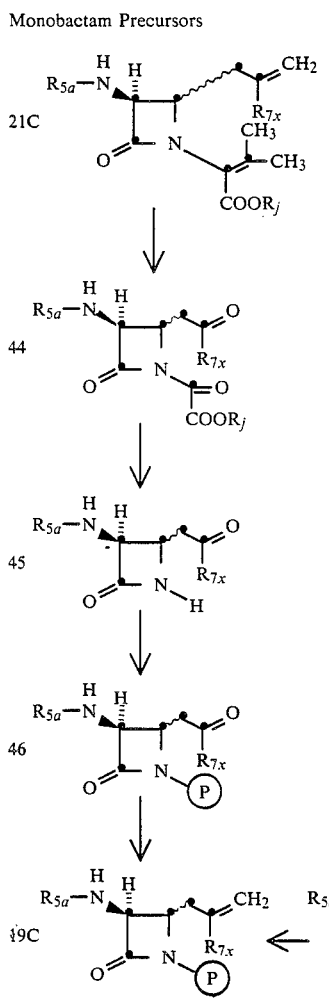

In the above Diagram R, $R_{5a}$ is as described above. $R_{7x}$ includes $R_7$ except the (protected carboxy)methyl group. $R_j$ is a carboxy protecting group as described for the above Scheme I. Ⓟ is an amino-protecting group as that is defined above for various compounds.

In the individual reactions of Diagram R, the N-(seco-penicillin)-4-(R,S)-(substituted or unsubstituted allyl)azetidinone (21C) is taken sequentially to the N-(glyoxamido)-4-(R,S)-((substituted or unsubstituted)-2'-oxoeth-1'-yl))azetidinone (44) and then to the free amine 4-(R,S)-((substituted or unsubstituted) 2'-oxoeth-1'-yl)azetidinone (45) with a one pot ozonolysis/methanolysis procedure used to convert similar compounds 21A to 41 to 37C in Route 3, Diagram O.

The 4-(R,S)-((substituted or unsubstituted) 2'-oxoeth-1'-yl)azetidinone (45) is converted to the corresponding amino-protected derivative (46) by standard amino-protecting group procedures, as discussed in the above McOmie and Greene references.

A standard Wittig reaction converts the amino-protected 4-(R,S)-((substituted or unsubstituted) 2'-oxoeth-1'-yl)azetidinone (46) to the corresponding 4-(R,S)-(substituted or unsubstituted allyl)azetidinone (19C). The Wittig procedure entails dissolving methyl bromide and triphenylphosphine in a dry aprotic polar solvent such as dimethylformamide, dimethylsulfoxide, tetrahydrofuran, or dimethoxyethane under a nitrogen atmosphere. A strong base, such as N-butyllithium or sodium hydride, is added to the cooled solution and the solution is stirred from $-20°$ C. to about $25°$ C. for 0.5 to 2.0 hours. The substrate is added and the solution is heated to effect the Wittig reaction.

An alternative Route to product compound 19C starts with product compound 17C. The free amine 4-(R,S)-(2-substituted or unsubstituted allyl)azetidinone (17C) is converted to the amino-protected derivative (19C) by standard amino-protecting group procedures.

(2) Monobactams: Final Products

Product compound 19C from the above precursor synthesis taken on to monobactam-like final products (VII, 50). The synthesis of these final products proceeds as follows:

(1) side chain cleavage at the C-3 nitrogen;
(2) reacylation of the C-3 amino group with an urethan-forming amino-protecting group;
(3) sulfonation of the azetidinone ring nitrogen;
(4) deprotection of the C-3 amino group; and
(5) reacylation of the C-3 amino group with an 2-(2'-aminothiazol-4-yl)-2-(Z-alkoxyimino)acetyl moiety.

In the following Diagram, all compounds are indicated to be a diastereomeric mixture at C-4. One skilled in the art will appreciate that the diastereomers of these compounds can be separated at any stage and used to give the preferred (3S,4S)-isomer of monobactam.

The synthesis of monobactam final products is outlined below in Diagram S:

Monobactam: Final Products            Diagram S

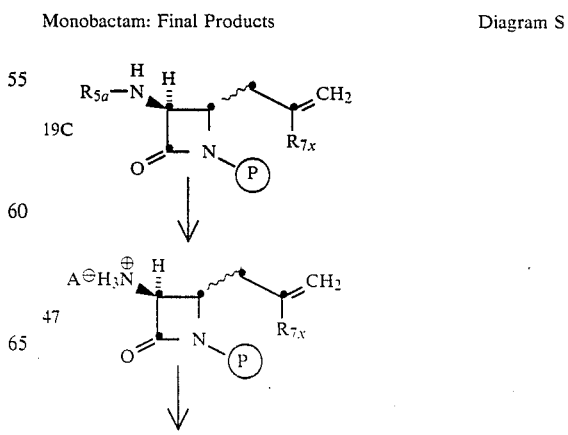

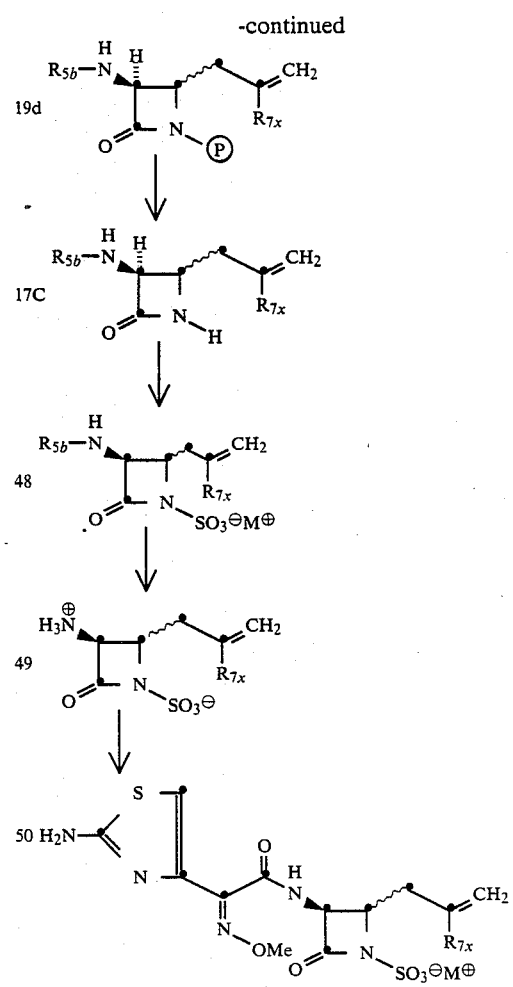

The term "A⁻" stands for an anion such as the chloride or bromide anion. The term "M+" represents an organic or inorganic cation such as the sodium ion, the potassium ion, or the tetra(n-butyl)ammonium ion. ⓟ, $R_{7a}$, $R_{5a}$ are as defined above for Diagram R. $R_{5b}$ represents $R_5$ when $R_f$ is only $C_1$ to $C_6$ alkoxy, allyloxy, phenoxy, benzyloxy, or 4-methyloxybenzyloxy.

Turning to the specific reactions of Diagram S, the amino-protected 4-(R,S)-(substituted or unsubstituted allyl)azetidinone (19C) is converted to the nucleus 3-(S)-amino-4-(R,S)-(substituted or unsubstituted allyl)azetidinone amine salt (47) using a standard penicillin or cephalosporin side chain cleavage reaction. One such reaction uses triphenylphosphite·chlorine· pyridine kinetic complex, followed by cleavage of the imino chloride thus formed with hydrogen chloride gas and isobutanol. This reaction is analogous to the one described for the conversion of compound 3 to compound 4 in Diagram A above.

The 3-(S)-amino-4-(R,S)-(substituted, unsubstituted allyl)azetidinone amine salt (47) is reacylated with a urethan-forming amino-protecting group to give the corresponding 3-(S)-urethan-4-(R,S)-(substituted or unsubstituted allyl)azetidinone (19D). The allyloxycarbonyl, alkyloxycarbonyl, phenoxycarbonyl, benzyloxycarbonyl, etc. groups are acylated onto the 3-(S)-amino nucleus using standard acylation techniques, especially those techniques used for forming urethan amino-protecting groups. For instance, di-(t-butyl)dicarbonate and the starting material (19D) are combined in tetrahydrofuran followed by the immediate addition of sodium bicarbonate. This reaction is analogous to the acylation of compound 4 to give compound 5, Diagram A, above.

The amino-protected 4-(R,S)-(substituted or unsubstituted allyl)azetidinone (19D) is deprotected to give the corresponding free amine compound (17C). The amino-protecting group is removed with standard removal methods, as long as these methods do not result in the simultaneous cleavage of $R_{5b}$. For instance, the removal of the azetidinone ring amino-protecting group using acid hydrolysis conditions would also rupture a t-butyl urethan group at the C-3 positon of the azetidinone.

The free amine 4-(R,S)-(substituted or unsubstituted allyl)azetidinone (17C) is sulfonated to give the corresponding N-(sulfonate salt)azetidinone (48). Typical sulfonation conditions involve dissolving a base in aprotic polar solvent (e.g. picoline in dichloromethane) under nitrogen. The solution is cooled to a low temperature (e.g. 0° C.) and chlorosulfonic acid is added. A methylene chloride solution of the substrate (17C) is added dropwise to the cooled reaction mixture and the mixture is stirred at 0° C. for 2 to 3 days. The mixture is then neutralized and a counter ion, for example, tetrabutylammonium hydrogen sulfate, is added to form the sulfonate salt.

The urethan side chain at the C-3 position of the N-(sulfonate salt)-4-(R,S)-(substituted or unsubstituted allyl)azetidinone (48) is cleaved to give the corresponding N-(sulfonate)-3-(S)-amino-4-(R,S)-(substituted or unsubstituted allyl)azetidinone zwitterion (nucleus) compound (49). The cleavage of the urethan group at the C-3 position is accomplished using standard amino-protecting group removal conditions. For example, when $R_{5b}$ is the t-butoxycarbonyl group, the substrate (48) is dissolved in formic acid and stirred until the reaction is essentially complete, typically requiring 4 hours.

The zwitterion compound from above (49) is acylated to give the monobactam derivative N-(sulfonate salt)-3-(S)-(2-(2'-aminothiazol-4'-yl)-2-(Z-methoxyimino)acetamido)-4-(R,S)-(substituted or unsubstituted allyl)azetidinone (50). The zwitterion is acylated using standard acylating conditions, such as with the side chain as the acid chloride, a mixed acid anhydride, or as the free acid in the presence of a dehydrating agent such as dichyclohexylcarbodiimide. For example, the zwitterion (49) is placed in a polar solvent mixture such as 2:1 acetone:water, and the pH of the resultant solution is adjusted to render the 3-(S)-amino group nucleophilic. Typically the pH of the solution is taken to 9. The isobutyl mixed anhydride derivate of the 2-(2'-aminothiazol-4'-yl)-2-(Z-methoxyimino)acetyl group is added and the reaction stirred until essentially complete. Compound 50 is isolated as the salt of the base that is used to raise the pH of the substrate solution.

The final products of the above synthetic routes the carbapenem compounds (VI) and the monobactam compounds (VII), are antibiotics. For example, a carbapenem of formula VI wherein $R_5$ was phenoxyacetyl, $R_6$ was hydrogen, $R_y$ was methyl, and X was acetoxy, showed activity against a strain of Micrococcus luteus and a strain of Bacillus subtilis in a standard disc plate assay.

Monobactam compounds of the formula VII are known to have activity against a variety of gram-positive and gram-negative bacteria and also known to possess β-lactamase inhibitory activities. A discussion of these bilogical properties for the compounds of formula VII can be found in U.K. Patent Application No. 2,091,724 A, published Aug. 4, 1982.

V. Experimental Section

In the following Experimental Section, the abbreviations THF, DMF, DME, AIBN and mmol stand for tetrahydrofuran, dimethylformamide, 1,2-dimethoxyethane, 2,2'-Azo bis(2-methylpropionitrile) and millimole, respectively.

The abbreviations i.r. and n.m.r. stand for infrared spectra and nuclear magnetic resonance spectra, respectively. In addition, the absorption maxima listed for the i.r. spectra are only those of interest and not all of the maxima observed.

In conjunction with the n.m.r. spectra, the following abbreviations are used: "s" is singlet, "d" is doublet, "dd" is doublet of doublets and "br.s" is broad singlet, "br" is broad absorption, "t" is triplet, "q" is quartet, and "m" is multiplet. "DMSO-$d_6$" is dimethyl sulfoxide where all protons have been replaced with deuterium.

The n.m.r. spectra were obtained on either a Varian Associates EM-390 90 MHz, a Jeol FT 90Q or a Bruker WM-270 instrument. The chemical shifts are expressed in δ values (parts per million downfield from tetramethylsilane).

The following Examples and Procedures are supplied to further illustrate the invention and are not meant to limit the scope of it in any fashion. The Examples and Procedures are divided into the three parts, roughly corresponding to the divisions of the discussion in the Detailed Description section, above.

EXAMPLES AND PROCEDURES (A) Starting Materials

PREPARATION 1

(Prop-1-en-3-yl)(tri-n-butyl)tin

Under a nitrogen atmosphere, magnesium (24 g), iodine (100 mg) and diethyl ether (400 ml) were combined. The solution was stirred until the iodine color had dissipated. A solution of allyl bromide (52 ml, 72.6 g, 0.6 mol) in diethyl ether (50 ml) was added to the solution in a dropwise manner over a 30 minute period. The solution was refluxed for an additional hour then cooled to room temperature. Bis(tri-(n-butyl))tin oxide (119 g, 0.2 mol) was dropped into the solution over a 1 hour period. The resultant reaction mixture was refluxed for 1.5 hours then was allowed to stand overnight at room temperature. The reaction mixture was cooled in an ice bath then saturated aqueous ammonium chloride solution was dropped in until no more heat was evolved. The resultant reaction mixture was poured onto ice then extracted with Skelly-B petroleum ether (2x, approximately 1.75 l. total). The combined organic layers were washed with saturated aqueous ammonium chloride solution, saturated aqueous sodium chloride solution, dried over magnesium sulfate, filtered with a filtering aid and concentrated in vacuo to give 126 g of light yellow oil. The product was distilled at 5 mm pressure and the product-containing fractions (collected at temperatures of 134°–145° C.) were combined to give 116 g, 88% yield of (prop-1-en-3-yl)(tri-(n-butyl))tin: n.m.r. (90 MHz, CDCl$_3$) δ 0.72–1.08 (n-butyl groups), 1.08–1.68 (m, n-butyl groups), 1.76 (d, C-3 protons of ally group), 4.5–4.92 (m, sp$^2$ protons of allyl group), 5.88 (m, sp$^2$ protons of allyl group).

PREPARATION 2

Methyl ((3-exomethylene)butan-4-yloate)(tri-(n-butyl))tin

Methyl (p-(t-toluenesulfonate))(3-exomethylene)-butanoate(20.10 g, 74.91 mmol), AIBN (6.41 g), toluene (149.5 ml) and tri-(n-butyl)tin hydride (approximately 42.5 ml) were combined under an argon atmosphere. The reaction mixture was stirred and illuminated with a sun lamp at a distance of 1 centimeter from the flask for 34 minutes. The mixture was diluted with ethyl acetate then concentrated in vacuo and the resultant pale yellow liquid and white solid were refrigerated. The crude mixture was chromatographed twice on activity 3 neutral alumina that was packed in hexane. The column was first eluted with hexane then a 3.5% ethyl acetate/hexane solution. The product-containing fractions were combined to yield 20.40 g of a colorless oil of methyl ((3-exomethylene)butån-4-yloate)(tri-(n-butyl))tin: n.m.r. (90 MHz, CDCl$_3$) δ 0.72–1.02 (n-butyl groups), 1.02–1.72 (m, n-butyl groups), 1.84 (d, sp$^3$ protons of butanyloate group), 2.96 (d, sp$^3$ protons of butanyloate group), 3.68 (s, methyl protons of ester group), 4.58 (sp$^2$ protons of 3-exomethylene group), 4.68 (sp$^2$ protons of 3-exoemthylene group).

PREPARATION 3

N-(Benzyl 3'-methylbut-2'-en-2'-yloate)-4-(S)-acetoxy-3-(S)-(phenoxyacetamido)azetidinone Under a nitrogen atmosphere, acetic acid (250 ml) was heated to 80° C. then combined with mecuric acetate (31.88 g, 100 mmol). Benzyl 6-(S)-(phenoxyacetamido)penicillinate (22.02 g, 50 mmol) was added and the resultant solution was stirred at 80° C. for 15 minutes. The reaction mixture was cooled to room temperature and suction-filtered. Most of the acetic acid was removed in vacuo and the concentrate was diluted with ethyl acetate, washed with water (4×), saturated aqueous sodium bicarbonate solution (2×), and brine (1×). The concentrate was then dried over magnesium sulfate, filtered and concentrated in vacuo to an orange oil. The oil was purified by preparatory scale liquid chromatography to give 15.8 g, 68% yield of N-(benzyl 3'-methylbut-2'-en-2'-yloate)-4-(S)-acetoxy-3-(S)-(phenoxyacetamido)azetidinone: n.m.r. (90 MHz, CDCl$_3$): δ 2.01 (s, 3, methyl protons of acetoxy group), 2.03 (s, 3, methyl group of seco-penicillin moiety), 2.33 (s, 3, methyl group of seco-penicillin moiety), 4.48 (s, 2, methylene of benzyl group), 5.03 (dd, 1, C-3 proton), 5.20 (s, 2, methylene of phenoxyacetamido group), 6.18 (d, 1, C-4 proton), 7.10 (br. m., 12, aromatic protons); i.r. (Neat): 1785 cm$^{-1}$ (β-lactam carbonyl only).

PREPARATION 4

4-(R,S)-Acetoxy-3-(S)-(phenoxyacetamido)azetidinone

N-(Benzyl 3'-methylbut-2'-en-2'-yloate)-4-(S)-acetoxy-3-(S)-(phenoxyacetamido)azetidinone (3.11 g, 6.67 mmol) was dissolved in aqueous acetone (27 ml acetone, 7 ml water). Potassium permanganate (a total of 2.92 g) was added portion-wise over a one our period to the stirred reaction mixture. The reaction mixture was filtered and concentrated in vacuo. To the concentrated solution was added a mixture of aqueous saturated sodium chloride solution and chloroform. The chloroform layer was separated and dried over magnesium sulfate, filtered and concentrated in vacuo. The concentrate was absorbed on silica gel-60 (10 g) and was chromatographed over an additional amount of silica gel-60 (20 g) using a gradient of hexane to 2:1 ethyl acetate/hexane. The product-containing fractions were evaporated in vacuo to give 1.32 g (71% yield) of 4-(R,S)-acetoxy-3-(S)-(phenoxyacetamido)azetidinone: n.m.r. (90 MHz, CDCl$_3$) δ 2.12 (s, 3), 4.24 (s, 2), b 4.95 (dd, 1, C-3 proton), 5.90 (d, 1, C-4 proton), 7.05 (br. m, 5, phenyl protons), 7.65 (d, 1, azetidinone ring nitrogen proton).

EXAMPLE 1

N-((t-Butyl)dimethylsilyl)-4-(R,S)-phenylselenyl-3-(S)-(phenoxyacetamido)azetidinone Under a nitrogen atmosphere, 4-(R,S)-acetoxy-3-(S)-(phenoxyacetamido)azetidinone (1.32 g, 4.74 mmol) was dissolved in melthylene chloride (9 ml). To this solution was added phenylselenol (1.5 ml, approximately 9.8 mmol), then boron trifluoride-etherate (10 drops). The resultant solution was stirred at room temperature for 20 minutes. The solution was diluted with ethyl acetate and extracted with saturated aqueous sodium bicarbonate solution (2×). The solution was dried over magnesium sulfate, filtered and concentrated in vacuo. The concentrate was absorbed onto silica gel (7 g) and then chromatographed over an additional amount of silica gel (15 g) using a gradient elution of toluene to ethyl acetate. The product-containing fractions gave 4-(R,S)-(phenylselenyl)-3-(S)-(phenoxyacetamido)azetidinone.

Under a nitrogen atmosphere, the above (phenylselenyl)azetidinone (4 mmol) was slurried in acetonitrile (15 ml). (t-Butyl)dimethylsilyl chloride (754 mg, 5 mmol) then triethylamine (0.7 ml, 5 mmol) was added to the slurry. The slurry was stirred for 2 hours then concentrated in vacuo. The concentrate was partitioned with a mixture of methylene chloride and 1N hydrochloric acid. The methylene chloride layer was dried over magensium sulfate, filtered and concentrated in vacuo. The latter concentrate was absorbed on silica gel (5 g) and chromatographed over additonal silica gel (12 g) eluting with a 15% ethyl acetate/toluene solution. The product-containing fractions were combined and taken to dryness in vacuo to give N-((t-butyl)dimethylsilyl)-4-(R,S)-phenylselenyl-3-(S)-(phenoxyacetamido)azetidinone: n.m.r. (90 MHz, CDCl$_3$) δ 0.39 (s, 3), 0.40 (s, 3), 1.05 (s, 9), 4.42 (s, 2), 4.60 (dd, 1, C-3 proton), 5.22 (d, 1, C-4 proton), 7.20 (br. m, 10, aromatic protons).

PREPARATIONS 5

3-(S)-3-phenylacetamido-3-methoxy-4-(R)-sulfinic acid)-N-(benzyl 3'-methylbut-2'-en-2'-yloate)azetidinone 7-(R)-7-Phenylacetamido-7-methoxy-3-methyl-3-cephem-4-carboxylate-1-sulfone (0.6 g, 1.23 mmol), ammonium chloride (0.33 g, 6.15 mmol), zinc (activated, 1.61 g, 24.6 mmol), DMF (15 ml), and water (10 ml) were combined under nitrogen. The reaction mixture was stirred at room temperature for 1.5 hours then additonal ammonium chloride (1 g) was added. Several hours later additional zinc was added. The mixture was stirred overnight at room temperature. The mixture was filtered and the filtrate was partitioned between ethyl acetate and 1N hydrochloric acid. The ethyl acetate layer was washed with 1N hydrochloric acid (1×) and brine (1×), dried over magnesium sulfate, filtered and concentrated in vacuo to give crude 3-(S)-phenylacetamido-b 4-(R)-(sulfinic acid)-N-(benzyl 3'-methylbut-2'-en-2'-yloate)azetidinone. The crude material was taken onto the next step without purification.

PREPARATION 6

3-(S)-3-phenylacetamido-3-methoxy-4-(R,S)-chloro-N-(benzyl 3'-melthylbut-2'-en-2'-yloate)azetidinone 3-(S)-3-phenylacetamido-3-methoxy-4-(R)-(sulfinic acid)-N-(benzyl 3'-methylbut-2'-en-2'-yloate)azetidinone (1.1 g, 2.42 mmol) and methylene chloride were combined under a nitrogen atmosphere. The solution was cooled to approximately −54° C. with an acetone/dry ice bath. t-Butylhypochlorite (0.31 ml, 2.73 mmol) was added to the solution with a syringe and the resultant mixture was stirred for 45 minutes. The mixture was diluted with ethyl acetate then extracted with 1N sodium thiosulfate, saturated aqeous sodium bicarbonate (2×) and brine (1×). The organic phase was dried over magnesium sulfate, filtered and evaporated to an oil to give 3-(S)-phenylacetamido-3-methoxy-4-(R,S)-chloro-N-(benzyl 3'-methylbuty-2'-en-2'-yloate)azetidinone: n.m.r. (90 MHz, CDCl$_3$) δ 2.15, 2.35 (s, 3 each, methyl protons of seco-penicillin group), 3.35 (s, 3, methoxy protons), 3.7 (s, 2, melthylene of phenylacetamido group), 5.38 (2, benzyl methylene protons), 5.72 (s, 1, C-4 proton), 7.32 (m, 10, aromatic protons).

PREPARATION 7

3-(S)-3-phenoxyacetamido-3-methoxy-4-(R)-sulfinic acid-N-(benzyl 3'-methylbut-2'-en-2'-yloate)azetidinone Benzyl 7-(R)-7-phenoxyacetamido-7-methoxy-3-methyl-3-cephem-4-carboxylate sulfone (5.95 g, 12.28 mmol), ethanol (300 ml) and methylene chloride (30 ml) were combined under nitrogen. Ammonium chloride (12 g, 224.3 mmol) and zinc (activated, 15.28 g, 233.7 mmol) were added and the mixture was stirred overnight at room temperature. The mixture was filtered through a celite filter bed then diluted with ethyl acetate. The filtrate was extracted several times with 1N hydrochloric acid, brine (1×), dried over magnesium sulfate, filtered and the organic phase was concentrated in vacuo to give 6.5 g of an oil of a mixture of 3-(S)-3-phenoxyacetamido-3-methoxy-4-(R)-(sulfinic acid)-N-(benzyl 3'-methylbut-2'-en-2'-yloate)azetidinone and the corresponding 3'-ene isomer: n.m.r. (90 MHz, CDCl$_3$) δ 2.35, 2.45 (s, 3 each, methyl protons of seco-penicillin moiety), 3.55 (s, 3, methoxy protons), 4.66 (s, 2), 5.25 (s), 5.4 (s, 2), 7.45 (m, 10, aromatic protons).

PREPARATION 8

3-(S)-3-phenoxyacetamido-3-methoxy-4-(R,S)-chloro-N-(benzyl 3'-methylbut-2'-en-2'-yloate)azetidinone 3-(S)-3-phenoxyacetamido-3-methoxy-4β-sulfinic acid-N-(benzyl 3'-methylbut-2'-en-2'-yloate)azetidinone (1.1 g, 2.42 mmol) and methylene chloride are combined under a nitrogen atmosphere. The solution is cooled to approximately −54° C. with an acetone/dry ice bath. t-Butylhypochlorite (0.31 ml, 2.73 mmol) is added to the solution with a syringe. The resultant solution is stirred for 45 minutes. The solution is diluted in ethyl acetate then is extracted with 1N sodium thiosulfate, saturated aqueous sodium bicarbonate (2×) and brine (1×). The organic phase is dried over magnesium sulfate, filtered and evaporated to an oil of 3-(S)-3-phenoxyacetamido- 3-methoxy-4-(R,S)-chloro-N-(benzyl 3'-methylbut-2'-en-2'-yloate)azetidinone.

EXAMPLE 2

3-(R)-phenoxyacetamido-4-(R,S)-(methylselenyl)azetidinone

Selenium powder (3.49 g, 44.2 mmol) was slurried in tetrahydrofuran (approximately 85.5 ml) under argon. Methyllithium (approximately 32.5 ml, 1.5M in diethyl ether) was added to the selenium slurry with a syringe. The resultant suspension was stirred for an additional 10 minutes then cooled to approximately −54° C. with a dry ice/acetone bath. A slurry of 3-(S)-phenoxyacetamido-4-(S)-acetoxyazetidinone (7.78 g, 28.0 mmol) in tetrahydrofuran (60 ml) was added to the cooled reaction mixture at a rate such that the temperature of the mixture did not exceed −48° C. The mixture was stirred for an additional 1 hour 18 minutes at a temperature of about −51° to about −42° C. A THF solution (30 ml) containing 3.4 ml of acetic acid was added to the mixture. The mixture was removed from the cooling bath, stirred for approximately 10 minutes then diluted with ethyl acetate. The mixture was washed with 1N hydrochloric acid (1×), saturated aqueous sodium bicarbonate (3×) and saturated aqueous sodium chloride (1×). The layers were separated and the combined aqueous layers were back-extracted with ethyl acetate (2×). The ethyl acetate extracts from the back-extraction were washed with saturated aqueous sodium chloride solution (1×). The ethyl acetate layers were combined, dried over magnesium sulfate, filtered and concentrated in vacuo to give 6.97 g of a yellow solid. The solid was dissolved in hot acetone, adsorbed onto silica gel-60 (28 g) and packed into a column containing an additional silica gel-60 (70 g). The column was eluted with a gradient of 30% ethyl acetate/hexane to 80% ethyl/acetate hexane. The elution was essentially stopped by crystallization of the compound. The column contents were emptied, stirred with methanol and the mixture was vacuum filtered. The filtrate was concentrated in vacuo to yield 3.73 g of a mixture of isomers of 3-(R)-phenoxyacetamido-4-(R,S)-(methylselenyl)azetidinone: n.m.r. (90 MHz, DMSO-d$_6$) δ 1.82 (s, methyl protons), 1.91 (s, methyl protons), 4.44 (s, methylene protons of phenoxyacetamido group), 4.49 (s, methylene proton of phenoxyacetamido group), 4.56–4.84 (m), 4.86–5.24 (m), 6.72–7.34 (m, aromatic protons), 8.48–8.96 (m, 1).

EXAMPLE 3

3-(R)-phenoxyacetamido-4-(R,S)-(phenylselenyl)azetidinone

Selenium powder (0.2385 g) was slurried in THF (6 ml) under argon. The phenyllithium (approximately 1.8 ml, 1.8M in 3:1 benzene:diethyl ether) was dropped into the solution over a 3 minute period. The solution was stirred for 20 minutes, then cooled to −78° C. in a dry ice/acetone bath. A slurry of 3-(S)-phenoxyacetamido-4-(S)-acetoxyazetidinone (0.5208 g, 1.872 mmol) and DMF (4 ml) was dropped in. The reaction mixture was stirred for approximately 3.2 hours, during which time the temperature rose to approximately −10° C. A mixture of acetic acid in tetrahydrofuran (approximately 26.5 ml total, approximately 0.2M) was added to the reaction solution then the reaction was removed from the cooling bath. The acidified mixture was diluted with ethyl acetate and washed with 1N hydrochloric acid (1×), saturated aqueous sodium bicarbonate solution (2×), saturated aqueous sodium chloride solution (1×), dried over sodium sulfate, filtered and concentrated in vacuo to give a yellow solid. The solid was dissolved in a hot acetone/methane mixture, absorbed onto silica gel-60 (approximately 4.1 g) and chromatographed through an additional silica gel-60 (7 g). The column was first eluted with toluene then with a 50% ethyl acetate/toluene solution to elute the product. The product-containing fractions were combined and concentrated in vacuo. The resultant solid was slurried in diethyl ether and collected by vacuum filtration. The solid was dried in a vacuum dessicator to yield 0.3259 g, 46% yield of 3-(R)-phenoxyacetamido-4-(R,S)-(phenylselenyl)azetidinone: n.m.r. (90 MHz, CDCl$_3$) δ 4.48 (s, methylene protons of phenoxyacetamido group), 4.54 (s, methylene protons of phenoxyacetamido group), 4.68 (dd, 1, C-3 proton of 4-(S)-isomer), 5.19 (d, 1, C-4 proton of 4-(S)-isomer), 5.35 (d, 1, C-4 proton of 4-(R)-isomer) 5.64 (m, 1, C-3 proton of 4-(R)-isomer), 6.2, 6.74–7.8 (m, 10, aromatic protons).

PREPARATION 9

3-(S)-phenoxyacetamido-4-(R,S)-acetoxyazetidinone 3-(S)-phnoxyacetamido-4-(S)-acetoxy-N-(benzyl 3'-methylbut-2'-en-2'-yloate)azetidinone (2.92 g, 7.48 mmol), acetone (33 ml), and deionized water (8 ml) were combined under nitrogen and stirred. Potassium permanganate (2.77 g, 17.5 mmol) was added in 5 approximately equal portions. The temperature rose after each addition of the permanganate and the temperature was allowed to return to approximately 25° C. before the next portion was added. After the addition of the final portion deionized water (1 ml) was added. The reaction mixture was suction filtered through paper. The filtrate was filtered through cotton and concentrated in vacuo. The concentrate was partitioned between chloroform and saturated aqueous sodium chloride solution. The aqueous phase was washed once with chloroform and the combined chloroform phases were dried over magnesium sulfate, suction filtered and evaporated in vacuo to give 2.18 g of a viscous yellow fluid. The yellow fluid was purified by flash chromatography through silica gel-60 (approximately 30 g). The yellow fluid was applied to the silica gel-60 column in methylene chloride and toluene solution then the column was eluted with the 2:1 mixture of ethyl acetate:hexane. The product-containing fractions were combined and evaporated in vacuo to yield 1.37 g of viscous brown fluid of 3-(S)-phenoxyacetamido-4-(R,S)-acetoxyazetidinone: n.m.r. (90 MHz, CDCl$_3$) 1.96 (s), 2.09 (s), 4.44 (s, methylene protons of phenoxyacetamido group), 4.48 (s, methylene protons of phenoxyacetamido group), 4.52 (s), 4.92 (dd, C-3 proton of 4-(S)-isomer), 5.56 (m, C-3 proton of 4-(R)-isomer, 5.86 (d, C-4 proton of 4-(S)-isomer), 5.94 (d, C-4 proton of 4-(R)-isomer), 6.04–6.72 (broad, proton), 6.72–7.52 (m, aromatic protons), 7.52–7.8 (br. d, nitrogen proton).

EXAMPLE 4

3-(R)-phenoxyacetamido-4-(R,S)-(phenylselenyl)azetidinone 3-(R)-phenoxyacetamido-4-(R,S)-acetoxyazetidinone (2.21 g, 7.94 mmol) and methylene chloride (14.5 ml) were combined and stirred under nitrogen. The solution was cooled in an ice/water bath and bis(tri-(methyl)-(silyl)trifluoroacetamide) (1.3 ml, 4.9 mmol) was added.

The flask was then warmed to room temperature and subsequently cooled in an ice/water bath. To the cooled solution was added phenylselenol (2.5 ml, 0.24 mmol). Boron trifluoride-etherate (0.5 ml, 4 mmol) was added and the solution was stirred for approximately 1 hour and 40 minutes, during which time the solution was allowed to slowly warm to room temperature. The solution was poured into ethyl acetate and the ethyl acetate layer was washed with saturated aqueous sodium bicarbonate solution (3×) and saturated aqueous sodium chloride solution (3×). The ethyl acetate layer was dried over magnesium sulfate, filtered and concentrated in vacuo to give 3.22 g of a wet yellow solid. The solid was slurried in methylene chloride and temporarily placed in the freezer under nitrogen. The white solid that remained in the slurry after addition of the methylene chloride was collected by filtration to give 0.55 g of an off-white crystalline mass. The methylene chloride filtrate was stored in the freezer. The filtrate was then combined with a filtrate from an identical procedure and purified on a silica gel-60 column. The combined filtrates were dissolved in additional methylene chloride and absorbed onto silica gel 60 (7 g). The absorbed filtrates were flash chromatographed over additional silica gel, eluting with a gradient of hexane to 55% ethyl acetate/hexane. The product-containing fractions were combined and evaporated in vacuo to yield 3-(R)-phenoxyacetamido-4-(R,S)-(phenylselenyl)azetidinone: n.m.r. (90 MHz, CDCl$_3$) $\delta$4.47 (methylene protons of phenoxyacetamido group), 4.53 (methylene protons of phenoxyacetamido group), 4.66 (dd, C-3 proton of 4-(S)- isomer) 5.17 (d, C-4 proton of 4-(S)- isomer), 5.32 (d, C-4 proton of 4-(R)- isomer), 5.61 (m, C-3 proton of 4-(R)- isomer), 6.25 (broad, nitrogen proton), 6.68–7.8 (m, aromatic protons).

EXAMPLE 5

3-(R)-phenoxyacetamido-4-(R,S)-(phenylselenyl)-N-(trimethylsilyl)azetidinone 3-(R)-phenoxyacetamido-4-(R,S)-(phenylselenyl)-azetidinone (0.73 g, 1.95 mmol) and THF (8 ml) were combined under nitrogen and the resultant solution was cooled in an ice/water bath. Trimethylsilyl chloride (0.37 ml, 2.9 mmol) was added by syringe followed by the addition of triethylamine (0.22 g, 2.2 mmol) and additional THF (2 ml). The mixture was stirred for 55 minutes, with additional THF (2 ml) added approximately 45 minutes after the stirring was started. The mixture was vacuum filtered to remove the solids that had formed. The solids were washed with toluene and the filtrate and the washes were combined. The combined organic layers were concentrated in vacuo to yield a viscous yellow-orange residue of 3-(R)-phenoxyacetamido-4-(R,S)-phenylselenyl-N-(trimethylsilyl)azetidinone.

PREPARATION 10

3-(S)-phenoxyacetamido-4-(S)-acetoxy-N-(methyl 3'-methylbut-2'-en-2'-yloate)azetidinone Toluene (300 ml), trimethylphosphite (38.75 ml, 328.60 mmol) and acetic acid (56.5 ml, 985.80 mmol) were combined under argon. The resultant mixture was heated to reflux and methyl 6-(S)-phenoxyacetamidopenicillinate-1-$\beta$-sulfoxide (50 g, 131.44 mmol) was added. The reaction mixture was refluxed for approximately 3 hours then concentrated in vacuo. The concentrate was diluted with ethyl acetate then washed with a pH 7 buffer (3X). The organic phase was dried over magnesium sulfate, filtered and concentrated in vacuo. This concentrate was dissolved in methylene chloride (250 ml). Triethylamine (10 ml) was added and the solution was stirred overnight. The solution was washed with 1N hydrochloric acid (2×) and the organic phase was concentrated in vacuo to give a mixture of crystals and oil. The crystals were triturated with methylethylketone the collected by vacuum filtration, washed with ether and dried. The crystalline material was 25.2 g of 3-(S)-phenoxyacetamido-4-(S)-acetoxymethyl-N-(methyl 3'-methylbut-2'-en-2'-yloate)azetidinone: n.m.r. (90 MHz, CDCl$_3$) $\delta$1.98 (s, 3, methyl protons of seco-penicillin moiety), 2.08 (s, 3, methyl of acetoxy group), 2.22 (s, 3, methyl protons of seco-penicillin moiety), 3.75 (s, 3, methyl of ester group), 4.52 (s, 2, methylene of phenoxyacetamido group), 5.05 (ABq, 1, C-3 proton), 6.18 (d, 1, C-4 proton), 7.1 (m, 5, aromatic protons).

PREPARATION 11

3-(S)-amino-4-(S)-acetoxy-N-(methyl 3'-methylbut-2'-en-2'-yloate)azetidinone

Methylene chloride (435 ml) was cooled to approximately −35° C. under argon. Chlorine gas was bubbled through the methylene chloride until a yellow color persisted. Triphenylphosphite was slowly added to the methylene chloride solution until the yellow color went away. Additional chlorine gas was bubbled through the solution until the yellow persisted and again the color was titrated away using triphenylphosphite. This procedure was repeated until all of the triphenylphosphite (37 ml) was used. An additional amount of triphenylphosphite (2 ml) was needed to remove the yellow color from the solution. During the addition of the triphenylphosphite, the temperature of the reaction solution was maintained from −35° C. to −15° C. After the last of the triphenylphosphite was added the solution was stirred at −35° C. for approximately 15 minutes.

3-(S)-phenoxyacetamido-4-(S)-acetoxy-N-(methyl 3'-methylbut-2'-en-2'-yloate)azetidinone (50 g, 128 mmol) then pyridine (11.52 ml) was added to the solution. The solution was stirred for 3 minutes at 0° C., the ice bath was removed and then the solution was stirred at room temperature for 100 minutes. The solution was cooled to −10° C. and hydrogen chloride gas was bubbled through it for approximately 30 seconds. Isobutyl alcohol (130.4 ml) was added and this solution was stirred for 1.5 hours. The solution was diluted with water, the layers separated and the aqueous phase was layered with ethyl acetate. The pH of the aqueous phase was adjusted to pH 8 by the addition of sodium hydroxide (5N and 1N). The organic phase from the reaction mixture and the aqueous phase were each washed with ethyl acetate (4X). The ethyl acetate washes were combined and concentrated in vacuo. The concentrate was dissolved in THF and concentrated in vacuo two times yielding an oil of 3-(S)-amino-4-(S)-acetoxy-N-(methyl 3'-methylbut-2'-en-2'-yloate)azetidinone hydrochloride salt. The crude product (oil) was used without further purification.

PREPARATION 12

3-(S)-((t-butyl)urethan)-4-(S)-acetoxy-N-(methyl-3'-methylbut-2'-en-2'-yloate)azetidinone 3-(S)-amino-4-(S)-acetoxy-N-(methyl 3'-methylbut-2'-en-2'-yloate)azetidinone hydrochloride salt (from the above Preparation 11), THF (300 ml) and di-(4-t-butyl)-dicarbonate (58 ml) were combined. Sodium bicarbonate (21 g) was added and the reaction mixture was stirred overnight at room temperature. The mixture was filtered through paper and the filtrate was diluted with ethyl acetate. The filtrate was washed with 1N hydrochloric acid (3×) and brine (1×) then concentrated in vacuo. The concentrate was chromatographed on silica gel using a gradient of toluene and ethyl acetate as the eluent. The product-containing fractions were combined and concentrated in vacuo to give 27.4 g of 3-(S)-((t-butyl)urethan)-4-(S)-acetoxy-N-(methyl 3'-methylbut-2'-en-2'-yloate)azetidinone: n.m.r. (90 MHz/CDCl$_3$) δ1.45 (s, 9, t-butyl group protons), 1.95 (s, 3, protons of methyl group of seco-penicillin moiety), 2.08 (s, 3, methyl protons of acetoxy group), 2.2 (s, 3, protons of methyl groups of seco-penicillin moiety), 3.78 (s, 3, methyl protons of ester), 5.3 (ABq, 1, C-3 proton), 6.08 (d, 1, C-4 proton).

PREPARATION 13

3-(S)-((t-butyl)urethan)-4-(S)-acetoxyazetidinone 3-(S)-((t-butyl)urethan)-4(S)-acetoxy-N-(methyl 3'-methylbut-2'-en-2'-yloate)azetidinone (19.5 g, 54.71 mmol) was dissolved in a methylene chloride/methanol mixture (480 ml) under nitrogen. The reaction mixture was cooled to −74° C. with an acetone/dry ice bath. Ozone was bubbled through the mixture until it was a faint blue color (36 minutes). The mixture was then purged with nitrogen. Dimethylsulfide (12 ml) was added and the mixture was allowed to warm to room temperature. To effect methanolysis of the resultant N-glyoxamido moiety, silica gel (approximately 20 g) was added and the mixture was stirred overnight. The mixture was filtered and evaporated to dryness to yield 18.31 g of crude product. The crude product and 19.82 g of identical crude product from an identical procedure were combined and absorbed onto silica gel. This material was chromatographed over additional silica gel, eluting first with a gradient of toluene (800 ml) and ethyl acetate (800 ml) then with an isocratic elution of 70% ethyl acetate/toluene. The product-containing fractions were combined and concentrated in vacuo to give 19.61 g of 3-(S)-((t-butyl)urethan)-4-(S)-acetoxyazetidinone: n.m.r. (90 MGz, CDCl$_3$) δ1.4 (s, 9, protons of t-butyl group), 2.08 (s, 3, methyl protons of acetoxy group), 4.6 (ABq, 1, C-3 proton), 5.78 (d, 1, C-4 proton), 7.3 (br. s, 1, N-H proton).

EXAMPLE 6

3-(R)-((t-butyl)urethan)-4-(R,S)-(methylselenyl)azetidinone

Selenium powder (3.13 g, 39.64 mmol) and THF (95 ml) were combined under nitrogen. Methyllithium (29.4 ml, 44.1 mmol) was added slowly to this solution and the resultant solution was cooled to −53° C. A solution of 3-(S)-((t-butyl)urethan)-4-(S)-acetoxyazetidinone (7 g, 28.66 mmol) and THF (55 ml) was dropped into the reaction solution. The temperature of the solution during the addition was kept below −45° C. The reaction solution was then stirred for 43 minutes at a temperature of between −45° C. and −53° C. Acetic acid (2M, 55 ml) in THF was added to quench the reaction. The cooling bath was removed and the solution was allowed to warm to room temperature. The solution was then diluted with ethyl acetate and washed with 1N hydrochloric acid (4×) and brine (1×). The organic phase was dried over magnesium sulfate, filtered and concentrated in vacuo. The concentrate (oil) was absorbed onto silica gel (approximately 20 g) and added to a column containing additional silica gel (70 g). The column was eluted with a gradient of 10% ethyl acetate/toluene to 60% ethyl acetate/toluene. The product-containing fractions were combined and concentrated in vacuo to give 5.7 g, 62.5% yield of 3-(R)-((t-butyl)urethan)-4-(R,S)-(methylselenyl)azetidinone: n.m.r. (90 MHz, CDCl$_3$) δ1.4 (s, 9, protons of t-butyl groupe, 2.05 (s, 3, methyl protons), 4.5 (ABq, 1, C-3 proton), 4.85 (d, 1, C-4 proton), 6.1 (s, 1, proton on azetidinone ring nitrogen).

EXAMPLE 7

3-(R)-((t-butyl)urethan)-4-(R,S)-(phenylselenyl)azetidinone

Selenium powder (1.03 g, 13.1 mmol) and THF (25 ml) were combined under argon. Phenyllithium (8 ml, 14.33 mmol) was dropped in and the resultant solution was cooled to −40° C. A solution of 3-(S)-((t-butyl)urethan)-4-(S)-acetoxyazetidinone (2 g, 8.19 mmol) in THF (20 ml) was dropped into the reaction solution. The temperature of the reaction solution was maintained between −45° C. to −35° C. during the addition of the azetidinone solution. A THF solution of acetic acid (12 ml, 2M) was added 15 minutes after the last addition of the azetidinone. The solution was then allowed to warm to room temperature and diluted with ethyl acetate. The solution was washed with 1N hydrochloric acid (3×), saturated aqueous sodium bicarbonate solution (1×) and brine solution (1×). The organic phase was dried over sodium sulfate, filtered and concentrated in vacuo to an oil. The oil was absorbed onto silica gel (8 g) then chromatographed over additional silica gel (20 g). The silica gel column was eluted with a gradient of toluene (600 ml) and 50% ethyl acetate/toluene (600 ml). The product-containing fractions were combined and concentrated in vacuo to give 2.55 g, 91.23% yield of 3-(R)-((t-butyl)urethan)-4-(R,S)-(phenylselenyl)azetidinone; n.m.r. (90 MHz, CDCl$_3$) δ1.42 (s, 9, protons of t-butyl group), 4.38 (ABq, 1, C-3 proton) 5.1 (m), 5.3 (m), 6.3 (s), 7.4 (m, 5, phenyl group protons).

B. The Process

EXAMPLE 8

N-((t-Butyl)dimethylsilyl)-4-(R,S)-(prop-1'-en-3'-yl)-3-(S)-(phenoxyacetamido)azetidinone Under a nitrogen atmosphere, N-((t-butyl)dimethylsilyl)-4-(R,S)-phenylselenyl-3-(R)-(phenoxyacetamido)azetidinone (550 mg, 1.12 mmol) was dissolved in benzene (3 ml). To the solution was added (prop-1-en-3yl)(tri-n-butyl)stannane (1.85 g, 5.6 mmol) then 2,2'-azobis (2-methylpropionitrile) (catalytic amount). The resultant solution was refluxed for 3 hours, allowed to cool to room temperature, diluted with methylene chloride and absorbed onto silica gel (7 g). The absorbed reaction mixture was chromatographed over additional silica gel (15 g) using a gradient elution of toluene to 30% ethyl acetate/toluene yielding 302 mg (72%) of a 1:1 mixture of 4-(R,S) isomers of N-((t-butyl)dimethylsilyl)-4-(R,S)-(prop-1'-en-3'-yl)-3-(S)(phenoxyacetamido)azetidinone: n.m.r. (90 MHz, CDCl$_3$) δ0.3 (2x s, 6, methyl groups of silyl group), 1.0 (s, 9, t-butyl protons of silyl group), 2.4 (br. m, 2, C-3 protons of allyl group), 3.8 (br. m, 1, C-3 proton), 4.42 (s, 2, methylene of phenoxyacetamido group), 4.95–5.9 (complex m, 4, C-4 proton and sp$^2$ protons of allyl group), 7.05 (m, 5, aromatic protons).

EXAMPLE 9

3-(R)-phenoxyacetamido-3-methoxy-4-(R,S)-(prop-1'-en-3'-yl)-N-(benzyl 3'-methylbut-2'-en-2'-yloate) azetidinone 3-(S)-phenoxyacetamido-3-methoxy-4-(R,S)-chloro-N-(benzyl 3'-methylbut-2'-en-2'-yloate)azetidinone (0.35 g, 0.76 mmol), (prop-1-en-3-yl)(tri-n-butyl)tin (2 ml), toluene (1.5 ml) and AIBN (catalytic amount) were combined under nitrogen. The reaction mixture was illuminated with a sun lamp for 2 hours, then partitioned between hexane and acetonitrile. The acetonitrile layer was washed several times with hexane then concentrated under vacuo to yield 3-(R)-3-phenoxyacetamido-3-methoxy-4-(R,S)-(prop-1'-en-3'-yl)-N-(benzyl 3'-methylbut-2'-en-2'-yloate)azetidinone: n.m.r. (90 MHz, CDCl$_3$). δ2.0 (s, 3, methyl group of seco-penicillin moiety), 2.24 (s, 3, methyl group of seco-penicillin moiety), 2.45 (m), 3.5 (s, 3, methoxy protons), 4.2 to 4.4 (2x s, 2 each, methylene protons of phenoxyacetamido group on each isomer), 5.0 (m), 5.12 to 5.2 (2x s, 2 each, methylene protons of benzyl group on each isomer), 5.7 (m), 7.2 (m, 10, aromatic protons).

EXAMPLE 10

3-(R)-phenylacetamido-3-methoxy-4-(R,S)-(prop-1'-en-3'-yl)-N-(benzyl 3'-methylbut-2'-en-2'-yloate)azetidinone 3-(S)-3-phenylacetamido-3-methoxy-4-(R,S)chloro-N-(benzyl 3'-methylbut-2'-en-2'-yloate)azetidinone (1.5 g, 3.28 mm) and. tolune (3 ml) were combined under nitrogen. AIBN (0.63 g, 3.28 mmol) and (prop-1-en-3-yl)(tri-(n-butyl))tin (5.90 ml, 3.28 mmol) were then added. The reaction mixture was illuminated with a sun lamp for 13 minutes. The mixture was diluted with acetonitrile and washed with hexane (4×). The combined hexane washings were extracted with acetonitrile and acetonitrile layers were combined and concentrated in vacuo to an oil. The oil was purified by flash chromatography over silica gel using an ethyl acetate to toluene gradient. The product-containing fractions were combined and concentrated to give 0.516 g of an oil of 3-(R)-3-phenylacetamido-3-methoxy-4-(R,S)-(prop-1'-en-3'-yl)-N-(benzyl 3'-methylbut-2'-en-2'-yloate)azetidinone: n.m.r. (90 MHz, CDCl$_3$) δ1.6 (s), 1.98 (s), 2.3 (m), 3.4 (s), 3.42 (m), 5.2 (s), 5.38 (s), 5.65 (m), 6.51 (s).

EXAMPLE 11

3-(S)-phenoxyacetamido-4-(R,S)-(prop-1'-en-3'-yl)azetidinone 3-(R)-phenoxyacetamido-4-(R,S)-(phenylselenyl-)azetidinone (1.40 g, 3.73 mmol), (prop-1-en-3-yl)(tri-(n-butyl))tin (3.59 g, 10.8 mmol), dimethoxyethane (8.0 ml) and AIBN (catalic) were combined under argon and the reaction mixture was heated to reflux with stirring. Throughout the course of the reflux, additional portions of AIBN (less 1 equivalent each) were added. The mixture was refluxed for 1 hour then concentrated in vacuo. The concentrated residue was partitioned between acetonitrile and hexane. The acetonitrile layer was washed with hexane (2×) and concentrated in vacuo to give 1.8696 g of crude yellow oil and crystals. The crude material was flash chromatographed through silica gel-60 (approximately 20 g) by first applying the crude material to the column with methylene chloride and secondly eluting the column sequentially with toluene and 75% ethyl acetyl/toluene. The product-containing fractions were combined and concentrated in vacuo to give 0.5344 g of yellow syrup. The syrup was an impure mixture 4-(R,S)-isomers of 3-(S)-phenoxyacetamidol-4-(R,S)-(prop-1'-en-3'-yl)azetidinone: n.m.r. (90 MHz, CDCl$_3$) δ2.04–2.84 (m), 3.58–3.82 (m), 3.82–4.10 (m), 4.52 (s x2, methylene protons of phenoxyacetamido group), 4.66 (dd, C-3 proton of 4-(S)-isomer), 4.94–5.3 (m), 5.3–6.04 (m).

EXAMPLE 12

3-(S)-phenoxyacetamido-4-(R,S)-[methyl (3'-exo-methylene)butan-4'-yloate]azetidinone 3-(R)-phenoxyacetamido-4-(R,S)-phenylselenyl-N-(trimethylsilyl)azetidinone (approximately 1.95 mmol), benzene (5 ml) and ((3-exomethylene)butan-4-yloate) (tri-(n-butyl)tin (1.65 g) were combined under nitrogen and the solution was heated to reflux. A slurry of AIBN (catalytic amount) and benzene was added to the solution. Additional amounts of the AIBN slurry was added periodically throughout the reaction. After approximately 2 hours and 40 minutes at reflux the reaction solution was allowed to cool and stored under nitrogen overnight. The solution was evaporated in vacuo and the residue was partitioned between acetonitrile and hexane. The acetonitrile was evaporated to dryness in vacuo and the residue was dissolved in toluene. The toluene solution was flash chromatographed through a silica gel-60 (11 g) column. The column was first eluted with hexane then with 50% ethyl acetate/toluene. The product-containing fractions were combined and evaporated to dryness in vacuo to yield 0.324 g of a yellow foam of 3-(S)-phenoxyacetamido-4-(R,S)-[methyl (3'-exomethylene)butan-4'-yloate]azetidinone: n.m.r. (90 MHz, CDCl$_3$) δ1.8–2.9 (m), 3.0 (s, C-2' methylene proton), 3.06 (s, C-2' methylene protons), 3.63 (s, methyl protons of 4-(R)-isomer), 3.66 (s, methyl protons of 4-(S)-isomer), 3.54–3.91 (m), 3.91–4.14 (m), 4.47 (s, methylene protons of phenoxyacetamido group of 4-(S)-isomer), 4.49 (s, methylene protons of phenoxyacetamido group of 4-(R)-isomer), 4.62 (dd, C-3 proton of 4-(S)-isomer), 4.91, 4.97 (overlapping s, exomethylene protons of 4-(R)-isomer and the 4-(S)-isomer, respectively), 5.32 (m, C-3 proton of 4-(R)-isomer), 6.51 (broad, nitrogen proton).

EXAMPLE 13

3-(S)-(t-(butyl)urethan)-4-(R,S)-(prop-1'-en-3'-yl)azetidinone 3-(R)-((t-butyl)urethan-4-(R,S)-methylselenyl-)azetidinone (4.3 g, 15.4 mmol), dimethoxyethane (43 ml) and (prop-1-en-3-yl)tri(n-butyl)tin (20.5 ml, approximately 61.6 mmol) were combined under nitrogen and the mixture was heated to a gentle reflux. AIBN (catalytic amount) was added and the mixture was refluxed for 35 minutes. Additional AIBN was added and the mixture was refluxed for an additional 16 minutes. The mixture was diluted with acetonitrile and was washed with hexane (4×). The acetonitrile layer was concentrated in vacuo to an oil. The oil was absorbed onto silica gel (15 g) then chromatographed over additional silica gel (60 g). The silica gel column was eluted with a gradient of toluene (1 1) and 60% ethyl acetate/toluene (1 1). The product-containing fractions were combined and concentrated in vacuo to give 1.44 g, 41.32% yield of 3-(S)-((t-butyl)urethan)-4-(R,S)-(prop-1'-en-3'-yl)azetidinone: n.m.r. (90 MHz, CDCl$_3$) δ1.41 (s, protons of t-butyl group), 1.86 (m), 3.64 (m, C-4 proton of 4-(S)-isomer), 3.83 (m, C-4 proton of 4-(R)-isomer), 4.28 (m, C-3 proton of 4-(S)-isomer), 4.88–5.48 (m, protons of double bond), 5.48–5.6 (m, protons of double bond), 6.08 (broad, nitrogen proton).

EXAMPLE 14

3-(S)-((t-butyl)urethan)-4-(R,S)-(prop-1'-en-3'-yl)azetidinone 3-(R)-((t-butyl)urethan-4-(R,S)-(phenylselenyl-)azetidinone (4 g, 11.72 mmol) and dimethoxyethane (40 ml) were combined under argon. (Prop-1-en-3-yt)tri(n-butyl)tin (16 ml, approximately 48 mmol) was added and the solution was heated to reflux. AIBN (catalytic amount) was added to the refluxing solution. The resultant solution was refluxed for 70 minutes and then allowed to cool to room temperature. The solution was diluted with acetonitrile then washed with hexane (4×). The acetonitrile layer was concentrated in vacuo to give an oil. The oil was absorbed onto silica gel (14 g) and chromatographed over an additional amount of silica gel (50 g). The silica gel column was eluted with a gradient of 1:3 ethyl acetate:toluene (800 ml) and 3:1 ethyl acetate/toluene (800 ml). The product-containing fractions were combined and evaporated in vacuo to give 1.75 g, 66% yield of 3-(S)-((t-butyl)urethan-4-(R,S)-(prop-1'-en-3'-yl)azetidinone: n.m.r. (90 MHz, CDCl$_3$) δ1.52 (s, 9, protons of t-butyl group), 2.5 (m), 3.8 (m), 4.4 (ABq, C-3 proton), 5.12 (m), 5.3 (m), 5.38 (s), 6.2 (s).

(C) Synthetic Uses

PREPARATION 14

3-(S)-phenoxyacetamido-4-(R,S)-[methyl (3'-keto)butan-4'-yloate]azetidinone 3-(S)-phenoxyacetamido-4-(R,S)-[methyl (3'-exomethylene)butan-4'-yloate]azetidinone (0.324 g, 0.975 mmol) and a mixture of 1:1 methanol:dichloromethane (9.6 ml) were combined under nitrogen and the solution was cooled in a dry ice/acetone bath. Ozone was bubbled through the solution until it was pale blue (approximately 3 minutes and 15 seconds). The solution was allowed to warm to room temperature. Dimethylsulfide (0.5 ml) was added and the resultant solution was stirred at room temperaturre for 17 minutes then concentrated in vacuo. The concentrate was 3-(S)-phenoxyacetamido-4l-(R,S)-[methyl (3'-keto)butan-4'-yloate]azetidinone: n.m.r. (90 MHz, CDCl$_3$) δ2.66–3.06 (m, s), 3.16–3.56 (m, s), 3.71 (s, methyl protons of 4-(R)isomer), 3.74 (s, methyl protons of 4-(S)-isomer), 3.6–4.0 (m), 4.20 (m), 4.50 (s, methylene protons of phenoxyacetamido group of 4-(S)-isomer), 4.55 (s, methylene protons of 4-(R)-isomer), 4.63 (dd, C-3 proton of 4-(S)-isomer), 5.16–5.4 (m), 6.4 (broad, nitrogen proton), 6.76–7.72 (m, aromatic protons).

PREPARATION 15

3-(S)-phenoxyacetamido-4-(R,S)-[methyl (3'-keto-2'-diazo)butan-4'-yloate]azetidinone 3-(S)-phenoxyacetamido-4-(R,S)-[methyl (3-keto)butan-4-yloate]azetidinone (0.975 mmol), acetonitrile (2.5 ml) and para-carboxyphenylsulfonazide (0.2264 g) were combined under nitrogen. Triethylamine (0.2956 g) was dropped into the solution and the solution was stirred at room temperature for approximately 16 minutes. The mixture was diluted with diethyl ether, washed with saturated aqueous sodium bicarbonate (3×) and saturated aqueous sodium chloride solution (2×). The diethyl ether layer was dried over magnesium sulfate, filtered and evaporated in vacuo to yield 0.381 g, of a viscous orange material. The material were purified on preparative thin layer chromatography plates using a 90% ethyl acetate/toluene solvent (triple elution). The silica gel from the plates was extracted with acetone. The acetone was filtered and the filtrate was evaporated in vacuo to give 3-(S)-phenoxyacetamido-4-(R,S)-[methyl (3'-keton-2'-diazo)butan-4'-yloate]azetidinone: n.m.r. (90 MHz, CDCl$_3$) δ2.86 (m, C-4' methylene proton of 4-(R)-isomer), 3.06 (m, C-4' methylene proton of 4-(S)-isomer), 3.58 (m, C-4' methylene proton of 4-(S)-isomer), 3.76 (s, methyl protons of ester group of 4-(R)-isomer), 3.81 (s, methyl protons of ester group of 4-(S)-isomer), 3.94 (m, C-4' proton of 4-(R)-isomer), 3.96 (m, C-4 proton of 4-(S)-isomer), 4.25 (m, C-4 proton of 4-(R)-isomer), 4.47 (s, methylene protons of phenoxyacetamido group of 4-(S)-isomer), 4.53 (s, methylene protons of phenoxyacetamido group of 4-(R)-isomer), 4.68 (dd, C-3 proton of 4-(S)-isomer), 5.31 (m, C-3 proton of 4-(R)-isomer), 6.34 (broad, nitrogen proton of 4-(R)-isomer), 6.55 (broad, nitrogen proton of 4-(S)-isomer), 6.72–7.4 (m, phenyl protons of 4-(S)-isomer), 6.77–7.39 (m, phenyl protons of 4-(R)-isomer), 7.44 (br. d, nitrogen proton of phenoxyacetamido group of 4-(S)-isomer), 7.50 (br. d, nitrogen proton of phenoxyacetamido group of 4-(R)-isomer).

PREPARATION 16

Methyl 5-(R,S)-6-(S)-phenoxyacetamido-3-keto-1-azabicyclo[3.2.0]heptan-7-one-2-carboxylate Rhodium diacetate dimer (catalytic amount) and benzene (9.0 ml) were combined and the mixture was heated to reflux with an oil bath. 3-(S)-phenoxyacetamido-4-(R,S)-[methyl (3'-keto-2'-diazo)butan-4'-yloate]azetidinone (0.2835 g, 0.7868 mmol) was added to the refluxing mixture with benzene (3.0 ml). The reaction mixture was refluxed for approximately 55 minutes and then stirred under nitrogen at room temperature. After approximately 19.5 hours and again after 50.5 hours, additional rhodium catalyst was added to the reaction mixture. After three days the mixture was filtered through activated charcoal with the aid of toluene. The filtrate was evaporated in vacuo to yield 0.1230 g of a light brown foam of methyl 5-(R,S)-6-(S)-phenoxyacetamido-3-keto-1-azabicyclo[3.2.0]heptan-7-one-2-carboxylate: n.m.r. (90 MHz, CDCl$_3$) δ2.39–3.15 (m), 3.77 (methyl protons of ester), 4.13 (m, C-5 proton of 5-(S)-isomer), 4.52 (s, methylene protons of phenoxyacetamido protons), 4.67 (s, C-2 proton of 5-(R)-isomer), 4.71 (s, C-2 proton of 5-(S)-isomer), 5.17 (dd, C-6 proton of 5-(S)-isomer), 5.4 (dd, C-6 proton of 5-(R)-isomer), 6.71–7.45 (m, phenyl protons), 7.57 (br. d, nitrogen proton).

PREPARATION 17

Methyl 5-(R,S)-6-(S)-phenoxyacetamido-3-acetoxy-1-azabicyclo[3.2.0]hept-2-en-7-one-2-carboxylate Methyl 5-(R,S)-6-(S)-phenoxyacetamido-3keto-1-azabicyclo[3.2.0]heptan-7-one-2-carboxylate (0.0643 g, 0.193 mmol) was dissolved in methylene chloride (1.3 ml) under argon. The solution was cooled in a wet ice bath. A methylene chloride solution of acetyl chloride (0.39 ml, 0.492M) was added followed by the addition of a methylene chloride solution of pyridine (0.43 ml, 0.449M). The resultant solution was stirred at 0° C. for approximately 1.5 hours then for an additional 1.5 hours at room temperature. The solution was diluted with methylene chloride and washed with pH 4 buffer (1×). 1,1,2-trichloroethane (TCE) was added and the solution was partially reduced in volumn in vacuo. This procedure was repeated twice, except the second time the solution was taken to dryness in vacuo. The residue was placed in a dry ice/acetone bath, dissolved in methylene chloride and stored overnight −78° C. The methylene chloride solution was streaked on 20 cm thin layer silica gel plates. The plates were developed in 50% ethyl acetate/toluene. The bands on the plates thus obtained were separately extracted with acetone and the product-containing bands were taken to dryness in vacuo to yield a mixture of C-5 position isomers of methyl 5-(R,S)-6-(S)-phenoxyacetamido-3-acetoxy-1-azabicyclo[3.2.0]hept-2-en-7-one-2-carboxylate: n.m.r. (90 MHz, CDCl$_3$) δ2.14 (s, methyl protons of acetoxy group), 3.68 (s, methyl protons of ester group), 3.76 (s, methyl protons of ester group), 4.52 (s, methylene protons of phenoxyacetamido group), 4.56 (s, methylene protons of phenoxyacetamido group), 4.3–5.08 (broad), 5.33 (dd, C-6 proton of 5-(S)-isomer), 6.34 (dd, C-6 proton of 5-(R)-isomer), 6.66 to 7.64 (m, aromatic protons).

PREPARATION 18

3-(S)-phenoxyacetamido-4-(R,S)-(1',2'-dihydroxyprop-3'-yl)-N-((t-butyl)dimethylsilyl)azetidinone 4-methylmorpholine-4-oxide (0.2804 g, 2.075 mmol) was dissolved in a mixture of deionized water (0.78 ml) and acetone (0.39 ml) under nitrogen. Osmium tetroxide (0.07 ml of a solution made up of 1 g of osmium tetroxide in t-butanol with a final volume of 50 ml) was added via a syringe. 3-(S)-Phenoxyacetamido-4-(R,S)-(prop-1'-en-3'-yl)-N-((t-butyl)dimethylsilyl)azetidinone (0.7306 g, 1.951 mmol) was transferred to the reaction solution with the aid of acetone (0.6 ml). The resultant solution was stirred at room temperature under nitrogen for approximately 2 hours and 20 minutes. The solution was diluted with ethyl acetate and then washed with 1N hydrochloric acid (2×) and brine (1×). The combined aqueous washes were back-extracted with ethyl acetate (2×). The organic extracts were combined and dried over sodium sulfate, filtered through celite then concentrated in vacuo to yield approximately 0.734 g, approximately 92% yield of 3-(S)-phenoxyacetamido-4-(R,S)-(1',2'-dihydroxyprop-3'-yl)-N-((t-butyl)dimethylsilyl)azetidinone: n.m.r. (90 MHz, CDCl$_3$) δ0.23 (methyl protons of silyl group), 0.94 (methyls of t-butyl group of silyl group, 1.12–2.16 (m), 2.96–4.21 (m), 4.46 (s, methylene protons of phenoxyacetamido group), 4.50 (s, methylene protons of phenoxyacetamido group), 4.68 (dd), 5–5.66 (m), 6.6–7.6 (m, aromatic protons), 8.12 (broad, nitrogen proton).

PREPARATION 19

3-(S)-phenoxyacetamido-4-(R,S)-(1'-oxoeth-2'-yl)-N-((t-butyl)dimethylsilyl)azetidinone 3-(S)-phenoxyacetamido-4-(R,S)-(1',2'-dihydroxyprop-3'-yl)-N-((t-butyl)dimethylsilyl)azetidinone (0.2298 g, 0.5624 mmol) was disssolved in distilled benzene (1.0 ml) under nitrogen. Lead tetraacetate (0.3747 g, 0.8451 mmol) was added and the solution was stirred for approximately 1 hour and 19 minutes. Ethylene glycol (approximately 0.02 ml) was added and the solution was stirred for an additional 10 minutes. The solution was centrifuged, the supernatant was removed, and the precipitate was suspended in fresh benzene and centrifuged again. The supernatant was again removed, and the precipitate was centrifuged a second time with benzene. The combined benzene washes were concentrated in vacuo to a syrup and solid. The syrup and solid were flash chromatographed through silica gel-60 (approximately 5 g). The crude material was applied to the column in toluene and the column was eluted with 40% ethyl acetate/toluene. The product-containing fractions were combined, concentrated in vacuo, then deuterochloroform was added to the residue and the resultant solution was evaporated in vacuo. The addition/evaporation of the residue in deuterochloroform was repeated several times. This procedure gave 0.0791 g of 3-(S)-phenoxyacetamido-4-(R,S)-(1'-oxoeth-2'-yl)-N-((t-butyldimethyl)silyl)azetidinone: n.m.r. (90 MHz, CDCl$_3$) δ0.24 (methyl protons of silyl group), 0.94 (s, methyl protons of t-butyl group of silyl group), 1.2–1.4 (m), 1.92–2.4 (m), 2.46–2.96 (m), 3.8–4.14 (m), 4.25 (m), 4.44 (methylene protons of phenoxyacetamido group), 4.64–4.88 (m), 5.16 (d), 6.0 (broad), 6.68–7.4 (m, aromatic protons), 9.69 (aldehydic proton).

PREPARATION 20

3-(S)-phenoxyacetamido-4-(R,S)-(1'-hydroxyeth-2'-yl)-N-((t-butyldimethyl)silyl)azetidinone 3-(S)-phenoxyacetamido-4-(R,S)-(1'-oxoeth-2'-yl)-N-((t-butyl)dimethylsilyl)azetidinone (0.530 g, 1.41 mmol) was dissolved in methanol (4 ml) under nitrogen. The solution was cooled in an ice bath then sodium borohydride (approximately 0.0496 g, 1.28 mmol) was added. The solution was stirred in an ice bath for 11 minutes then allowed to warm to room temperature. The solution was diluted with acetone then concentrated in vacuo to yield approximately 0.80 g of a yellow syrup. The syrup was flash chromatographed on silica gel-60 (approximately 10 g). The syrup was applied to the column as a methanol solution and the column was eluted with 60% ethyl acetate/toluene. The product-containing fractions were combined and evaporated in vacuo to yield 0.3294 g of an orange-yellow semi-solid. Some of the semi-solid (dissolved in methanol) was applied to 20 cm×20 cm thin layer chromatography plates. The plates were developed in a 10% methanol/wthyl acetate solution and the product-containing bands were isolated from the silica gel with methanol. The methanol extracts were filtered and concentrated in vacuo to give 3-(S)-phenoxyacetamido-4-(R,S)-(1'-hydroxyeth-2'-yl)-n-((t-butyl)dimethylsilyl)azetidinone: n.m.r. (90 MHz, CDCl$_3$) δ0.24 (s), 0.84 (s), 0.92 (s), 1.4–2.30 (m), 2.36 (s), 3.32–4.24 (m), 4.48 (methylene protons of phenoxyacetamido group), 4.60 (dd), 5.08-5.52 (m), 6.72-7.36 (m, aromatic protons).

PREPARATION 21

3-(S)-((t-butyl)urethan-4-(R,S)-(prop-1'-en-3'-yl)-N-(sulfonate)azetidinone tetrabutylammonium salt 2-Picoline (4.2 ml, 42.5 mmol) and methylenechloride (14 ml) were combined under nitrogen. The solution was cooled to 0° C. with a wet ice bath. Chlorosulfonic acid (1.42 ml, 21.36 mmol) was dropped in and the solution was stirred. After 30 minutes of stirring the ice bath was removed.

3-(S)-((t-butyl)urethan)-4-(R,S)-(prop-1'-en-3'-yl)azetidinone (1.83 g, 8.08 mmol) and methylene chloride (25 ml) were combined under nitrogen. To this azetidinone-containing solution was added a portion of the 2-picoline-chlorosulfonic acid solution (15 ml) from above. The reaction mixture was stirred for 70 hours then partitioned with 0.5N potassium dihydrogen phosphate solution. The aqueous phase was separated and the organic phase was washed once more with the potassium dihydrogen phosphate solution. All of the aqueous phases were combined and tetrabutylammonium hydrogen sulfate (3 g) was added to the aqueous phases. Methylene chloride was added to the aqueous solution and the pH of the resultant solution was adjusted to 6.6 by the addition of ammonia gas. The methylene chloride phase was isolated and concentrated to an oil in vacuo. The oil was twice dissolved in toluene and concentrated in vacuo to give 5.1 g of crude 3-(S)-((t-butyl)urethan)-4-(R,S)-(prop-1'-en-3'-yl)-N-(sulfonate)azetidinone tetrabutylammonium salt. The product was used without further purification.

PREPARATION 22

3-(S)-amino-4-(R,S)-(prop-1'-en-3'-yl)-N-(sulfonate)azetidinone zwitterion

Formic acid (50 ml) was added to 3-(S)-((t-butyl)urethan)-4-(R,S)-(prop-1'-en-3'-yl)-N-(sulfonate)azetidione tetrabutylammonium salt (5.1 g) and the resultant solution was stirred for approximately 4 hours. The reaction mixture ws then concentrated to approximately one-half of its volume in vacuo. Ethyl acetate (approximately 80 ml) was added to the concentrate and a white solid precipitated. The suspension was stirred for approximately 30 minutes and the resultant solids were collected by filtration to give 0.2456 g of 3-(S)-amino-4-(R,S)-(prop-1'-en-3'-yl)-N-(sulfonate)azetidinone zwitterion: n.m.r.(270 MHz, DMSO-$d_6$) $\delta$2.55 (m), 3.15 (m, 1, C-4 proton), 3.8 (m, 1, C-3 proton), 5.2 (m), 5.85 (m), 8.8 (br. s).

PREPARATION 23

3-(S)-(amino)-4-(R,S)-(prop-1'-en-3'-yl)-N-((t-butyl)dimethylsilyl)azetidinone hydrochloride salt Methylene chloride (100 ml) was cooled to -25° C. under nitrogen. Chlorine gas was bubbled through the cooled solvent until a medium yellow color persisted. Triphenylphosphite was added dropwise until the yellow color began to dissipate. When no more color persisted in the solution, additional chlorine gas was bubbled through until a yellow color persisted. Again the yellow color was titrated away by the dropwise addition of triphenylphosphite. At this point, a total of 5.77 ml (22 mmol) of triphenylphosphite had been added. A faint yellow color persisted and additional triphenylphosphite (0.2 ml) was added. The solution was then stirred at approximately -20° C. for 30 minutes. At this time part of the solution (approximately 56 ml) was transferred to a new, cool flask under argon. The solution was cooled to approximately -25° C. and a solution of 3-(S)-phenoxyacetamido-4-(R,S)-(prop-1'-en-3'-yl)-N-((t-butyl)dimethylsilyl)azetidinone (approximately 3.5 g, approximately 9.34 mmol) in methylene chloride (10 ml) was added. The substrate solution was rinsed into the reaction mixture with an additional amount of methylene chloride (5 ml). Pyridine (0.9 ml, 11 mmol) was dropped into the solution. The solution was removed from the ice bath for approximatly 15 minutes then placed back in back in the bath. The solution was then stirred for 3.5 hours at approximately 5° C. Isobutyl alcohol (65 ml) was added and ten minutes later hydrogen chloride gas was bubbled through the solution for 20 to 30 seconds. The solution was stirred at room temperature for an additional 2 hours and extracted with 1N hydrochloric acid. The pH of the solution was adjusted to 1. The aqueous phase was isolated and layered with ethyl acetate, the pH of the solution was adjusted to 7.5 and the ethyl acetate was removed in vacuo. The resultant residue was chromatographed over silica gel. The silica gel column was eluted with a mixture of 3:2:4:0.5 ethyl acetate:methanol:toluene:acetic acid. The product-containing fractions were combined and evaporated in vacuo to give 0.53 g of 3-(S)-amino-4-(R,S)-(prop-1'-en-3'-yl)-N-((t-butyl)dimethylsilyl)azetidinone hydrochloride salt: n.m.r. (90 MHz, CDCl$_3$) $\delta$1.0 (s, methyl protons of silyl group), 1.02 (s, t-butyl protons of silyl groups), 2.4 (m), 3.9 (m), 4.4 (m), 5.2 (m), 5.9 (m), 6.5 (m).

EXAMPLE 15

3-(S)-((t-butyl)urethan)-4-(R,S)-(prop-1'-en-3'-yl)-N-(t-butoxycarbonyl)azetidinone 3-(S)-amino-4-(R,S)-(prop-1'-en-3'-yl)-N-((t-butyl)dimethylsilyl)azetidinone hydrochloride salt (0.52 g, 1.88 mmol), THF (7 ml) and di-(t-butyl)dicarbonate (0.85 ml, approximately 3.6 mmol) was combined followed by the addition of 1N sodium hydroxide solution (5 ml). The reaction mixture was stirred for 1 hour at room temperature. The mixture was diluted with ethyl acetate and extracted with 1N hydrochloric acid (2×) and brine (1×). The organic phase was isolated and concentrated to an oil in vacuo. The oil was dissolved in methylene chloride and the solution was absorbed onto silica gel (4 g) and chromatographed over an additional 17 g of silica gel. The silica gel column was eluted with a gradient of toluene and 2:1 ethyl acetate:toluene. The product-containing fractions were combined and evaporated in vacuo to give an oil of 3-(S)-(t-butyl)urethan)-4-(R,S)-(prop-1'-en-3'-yl)-N-(t-butoxycarbonyl)azetindinone: n.m.r. (90 MHz, CDCl$_3$) $\delta$1.52 (methyl protons of t-butyl group), 2.5 (m), 3.8 (m), 4.4 (m), 5.2 (m), 5.8 (m), 6.3 (m).

I claim:
1. A compound of the formula

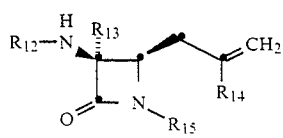

wherein
$R_{12}$ is an acyl group of the formula

wherein
$R_k$ is
(a) $C_1$ to $C_7$ alkyl, cyanomethyl or 4-protected amino-4-protected carboxybutyl; or
(b) $C_1$ to $C_6$ alkoxy, allyloxy, phenoxy, benzyloxy or 4-methoxybenzyloxy; or
(c) the group $R_1$, wherein $R_1$ is phenyl or substituted phenyl, wherein the substituents are one or two halogens, protected hydroxy, cyano, trifluoromethyl, $C_1$ to $C_4$ alkyl, $C_1$ to $C_4$ alkoxy, protected amino, protected carboxy, protected carboxymethyl, protected hydroxymethyl or protected aminomethyl; or
(d) an arylalkyl or aryloxyalkyl group of the formula

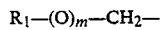

wherein $R_1$ is as defined above and m is 0 or 1; or
(e) a substituted arylalkyl or heteroarylalkyl group of the formula

wherein $R_m$ is $R_1$ as defined above, thien-2-yl, thien-3-yl, fur-2-yl, or fur-3-yl; and W is protected hydroxy, protected carboxy, or protected amino; or
(f) a heteroarylmethyl group of the formula

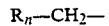

wherein $R_n$ is thien-2-yl, thien-3-yl, fur-2-yl, fur-3-yl, thiazol-2-yl, tetrazol-5-yl, or tetrazol-1-yl;
$R_{13}$ is hydrogen or methoxy;
$R_{14}$ is hydrogen, $C_1$ to $C_6$ alkyl or cycloalkyl, phenyl, phenyl ($C_1$ to $C_4$)alkyl or (protected carboxy)methyl; and
$R_{15}$ is hydrogen or an amino protecting group.

2. A compound of claim 1, wherein $R_{12}$ is an acyl group of the formula

wherein $R_k$ is an arylalkyl or aryloxyalkyl group of the formula

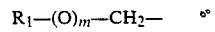

3. A compound of claim 2, wherein $R_1$ is phenyl.
4. A compound of claim 3, wherein $R_{14}$ is hydrogen or (protected carboxy)methyl.
5. A compound of claim 4, wherein $R_{15}$ is hydrogen, trimethylsilyl or t-butyl(dimethyl)silyl.
6. A compound of claim 5, wherein $R_{13}$ is hydrogen.

* * * * *

UNITED STATES PATENT AND TRADEMARK OFFICE
CERTIFICATE OF CORRECTION

PATENT NO. : 4,918,185

DATED : April 17, 1990

INVENTOR(S) : Larry C. Blaszczak

It is certified that error appears in the above-identified patent and that said Letters Patent is hereby corrected as shown below:

Abstract

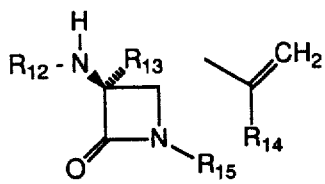 should read -- 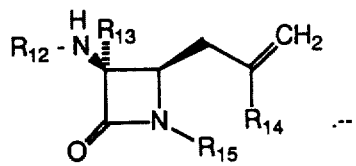 .--

Column 1, lines 38 thru 45

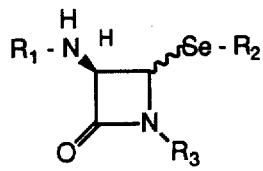 " should read -- 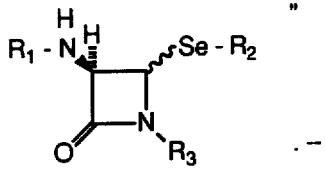 " .--

Column 1, lines 52 thru 58

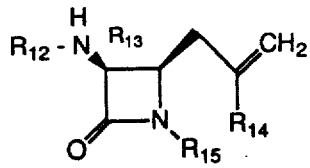 " should read -- 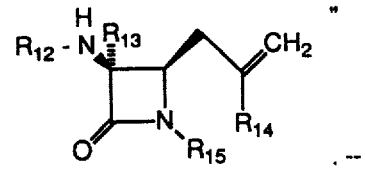 " .--

UNITED STATES PATENT AND TRADEMARK OFFICE
CERTIFICATE OF CORRECTION

PATENT NO. : 4,918,185
DATED : April 17, 1990
INVENTOR(S) : Larry C. Blaszczak

It is certified that error appears in the above-identified patent and that said Letters Patent is hereby corrected as shown below:

Column 2 lines 13 thru 18

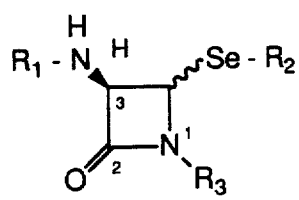   "   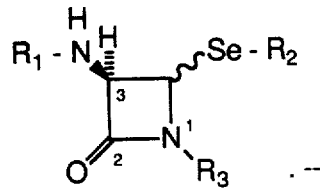   "

should read --                                              .--

Column 10, lines 23 thru 27

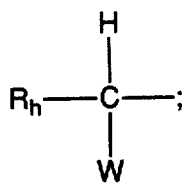   "   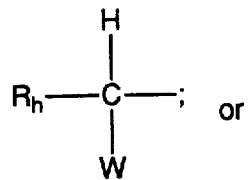  or should read --                                              .--

Column 10, line 30

$R_2$——$CH_2$——   should read --   "  $R_i$——$CH_2$——  "  .--

UNITED STATES PATENT AND TRADEMARK OFFICE
CERTIFICATE OF CORRECTION

PATENT NO. : 4,918,185

DATED : April 17, 1990

INVENTOR(S) : Larry C. Blaszczak

Page 3 of 5

It is certified that error appears in the above-identified patent and that said Letters Patent is hereby corrected as shown below:

Column 12, lines 10 thru 15

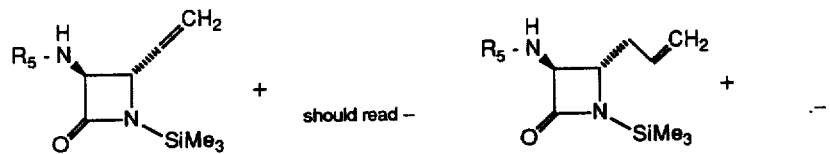

Column 25, lines 60 thru 68

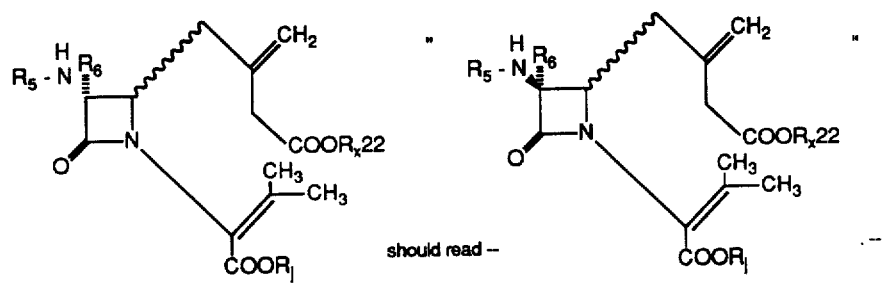

Column 41, lines 7 thru 12

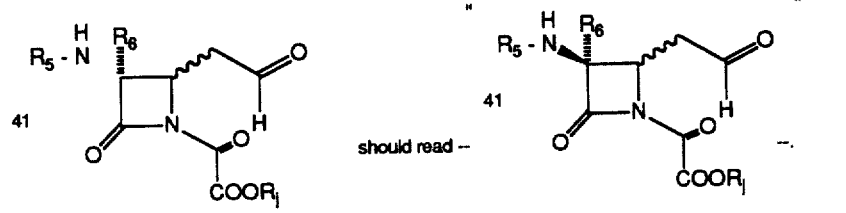

UNITED STATES PATENT AND TRADEMARK OFFICE
CERTIFICATE OF CORRECTION

PATENT NO. : 4,918,185                           Page 4 of 5
DATED      : April 17, 1990
INVENTOR(S): Larry C. Blaszczak It is certified that error appears in the above-identified patent and that said Letters Patent is hereby corrected as shown below:

Column 45, lines 1 thru 15

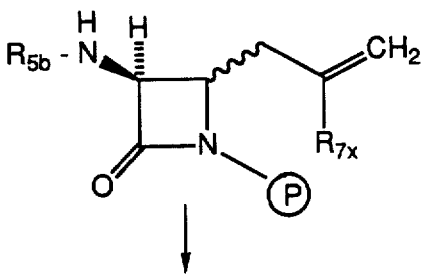

19d

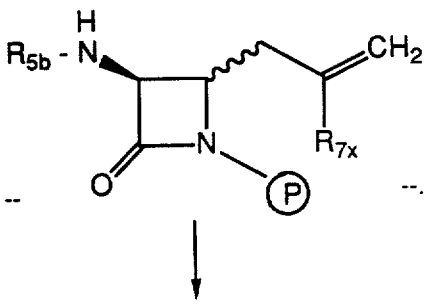

19d should read --

UNITED STATES PATENT AND TRADEMARK OFFICE
CERTIFICATE OF CORRECTION

PATENT NO. : 4,918,185  Page 5 of 5
DATED : April 17, 1990
INVENTOR(S) : Larry C. Blaszczak It is certified that error appears in the above-identified patent and that said Letters Patent is hereby corrected as shown below:

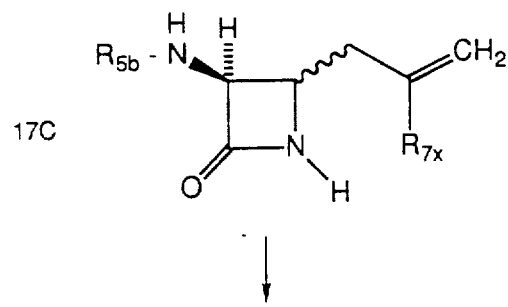 " 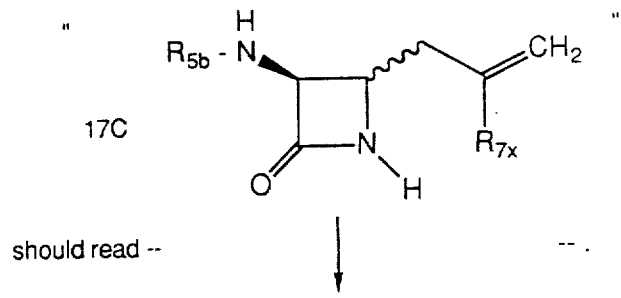 "

should read --                                                          -- .

Signed and Sealed this

Third Day of December, 1991

Attest:

HARRY F. MANBECK, JR.

*Attesting Officer*          *Commissioner of Patents and Trademarks*